(12) United States Patent
Chang

(10) Patent No.: US 10,307,586 B2
(45) Date of Patent: Jun. 4, 2019

(54) SYSTEM AND METHOD FOR RELIEVING HIGH BLOOD SUGAR FACTOR OF DIABETES

(71) Applicant: Wen-Chieh Chang, Taichung (TW)

(72) Inventor: Wen-Chieh Chang, Taichung (TW)

(73) Assignee: Taiwan Resonant Waves Research Corp., Taipei (TW)

( * ) Notice: Subject to any disclaimer, the term of this patent is extended or adjusted under 35 U.S.C. 154(b) by 150 days.

(21) Appl. No.: 15/291,084

(22) Filed: Oct. 12, 2016

(65) Prior Publication Data
US 2017/0312506 A1    Nov. 2, 2017

(30) Foreign Application Priority Data
Apr. 28, 2016   (CN) .......................... 2016 1 0277731

(51) Int. Cl.
| A61N 1/04 | (2006.01) |
| A61N 1/32 | (2006.01) |
| A61N 1/36 | (2006.01) |

(52) U.S. Cl.
CPC ........... *A61N 1/32* (2013.01); *A61N 1/36034* (2017.08); *A61N 1/0492* (2013.01); *A61N 1/3606* (2013.01)

(58) Field of Classification Search
CPC ........ A61N 1/32; A61N 1/36034; A61N 1/36; A61N 1/05; A61N 1/0492; A61N 1/3606
See application file for complete search history.

(56) References Cited

U.S. PATENT DOCUMENTS

| 4,850,959 | A | 7/1989 | Findl |
| 5,231,988 | A | 8/1993 | Wernicke et al. |
| 6,424,864 | B1 | 7/2002 | Matsura |
| 10,029,114 | B2 * | 7/2018 | Chang .................. A61N 5/0613 |
| 10,065,033 | B2 * | 9/2018 | Chang ...................... A61N 1/32 |
| 10,118,033 | B2 * | 11/2018 | Chang ...................... A61N 1/32 |
| 10,220,206 | B2 * | 3/2019 | Chang ................ A61N 1/36014 |
| 2007/0142753 | A1 | 6/2007 | Warlick et al. |
| 2015/0032178 | A1 | 1/2015 | Simon et al. |
| 2016/0121113 | A1 | 5/2016 | Chang et al. |
| 2017/0021172 | A1 * | 1/2017 | Perez ................. A61N 1/37235 |

FOREIGN PATENT DOCUMENTS

| CA | 2311666 | 9/2007 |
| CN | 1280514 A | 1/2001 |
| CN | 103212159 A | 7/2013 |
| CN | 104117147 A | 10/2014 |
| TW | 201343215 A | 11/2013 |
| TW | I453046 B | 9/2014 |
| TW | 201529118 A | 8/2015 |
| TW | M511871 | 11/2015 |
| TW | 201603776 A | 2/2016 |
| WO | WO2013040432 A1 | 3/2013 |

* cited by examiner

*Primary Examiner* — Paula J Stice

(57) ABSTRACT

A system and method for relieving high blood sugar factor of diabetes includes an energy wave generator with an energy wave's frequency control mode. The energy wave's frequency control mode includes multiple controls for controlling and generating energy waves with corresponding energy densities to effect on diabetic patient's body, so as to reduce and eliminate the high blood sugar factors of the diabetic patient.

16 Claims, 12 Drawing Sheets

FIG. 4

SYSTEM AND METHOD FOR RELIEVING HIGH BLOOD SUGAR FACTOR OF DIABETES

CROSS-REFERENCE TO RELATED APPLICATION

This non-provisional application claims priority of Patent Application No. CN201610277731.x, filed in P.R. China on Apr. 28, 2016.

BACKGROUND OF THE INVENTION

1. Fields of the Invention

The present invention relates to a system and method for relieving high blood sugar factor of diabetes, and more particularly, to a technology for controlling and emitting electric energy waves to treat high blood sugar factor of diabetes.

2. Descriptions of Related Art

Diabetes is a serious metabolic disorder. If the secretion of insulin in a human body is insufficient, glucose will be unable to enter into cells or used by the cells, so that the glucose content in bood will be increased, and the metabolic disorder may occur. According to the standard set by American Diabetes Association, diabetes is diagnosed by meeting any one of the following conditions: 1) Fasting Plasma Glucose (FPG) is measured to be 7.0 Mmol/liter (126 mg/dl) or higher; 2) In the oral glucose tolerance test (OGTT), the plasma glucose is measured to be 11.1 Mmol/liter (200 mg/dl) or higher after orally taking 75 g of glucose for 2 hours; 3) In a random plasma glucose, the plasma glucose is measured to be 11.1 Mmol/liter (200 mg/dl) or higher, and the patient has high blood glucose symptoms; and 4) The glycated hemoglobin (HbA1C) is measured to be 6.5 or higher. If the level of human blood glucose is too high, glucose will be unable to be absorbed by kidney, so that the glucose will be discharged together with urine. If the urine contains a relatively large quantity of sugar, then diabetes will be developed. At present, there are two main methods used by Western medicine to treat diabetes: 1. Insulin Injection (Supplement insulin by injection), and Oral Medication (Control blood sugar by taking medicine orally). Although the aforementioned treatments can improve insulin secretion and lower insulin resistance to control the high blood sugar factor of a patient, yet these treatments can just control the blood sugar of diabetes only, but cannot cure diabetes. If a patient stops the insulin injection or oral medication, different complications of diabetes may occur. Furthermore, the aforementioned injection method is an invasive allopatic treatment, so that the patient's kidney may be injured easily after a long-term treatment, and ultimately the patient requires dialysis.

As to the treatment of diabetes by Chinese medicine, R.O.C. Pat. No. I356706 entitled "Chinese herb capable of controlling metabolic syndromes" has disclosed a composition of bidens and ginseng with the effects of promoting the secretion of insulin and reducing the resistance of insulin. Although the conventional treatment can regulate the value of human blood sugar, this treatment is still an oral medication treatment, so that it is generally considered as an indirect invasive treatment, and its potency has a chemical restraint effect on human body. Under the long-term oral medication treatment, the patient's kidney may be injured or damaged easily.

According to the theory of quantum medicine, all living things and life forms have their own physiological frequency (which is the biological resonant wave), and harmonized wave frequency occurs in healthy human bodies. On the other hand, a disordered wave frequency occurred in human body indicates functional degradation of the living thing and sickness caused by a harmonic interference of diseases or viruses. In 1930, American physicist, Royal Rife, discovered that every object contains bacteria and viruses having their own natural frequency, and such discovery was used by doctors of University of Southern California for medical tests in 1934 and satisfactory results were achieved. Royal Rife's research discovered that different resonant waves have different physiological reactions to human body. Thereafter, a Canadian corporation, Resonant Light Technology Inc. developed a resonant wave health instrument for measuring the physiological frequency of a human body. The electric energy wave emitted from the instrument has a wavelength of 4~20 microns (um), which is very close to the wavelength of the biological wave of a human body (3~45 um), so as to provide a healthcare function to human body. At present, researches on the subject of treating cancers by electromagnetic waves are conducted extensively. Although the prior art has introduced electric energy waves into human body to produce resonance with the physiological frequency of human body, so as to achieve the treatment effect, yet the conventional techniques or researches do not use the electric energy wave technology to create a frequency modulation treatment formulation for reducing or eliminating high blood sugar factor of diabetes to cure diabetes effectively.

Since the biological resonant waves probably have high efficacy in curing human diseases, and the inventor of the present patent application has researched for a long time to apply the electric energy wave to reduce or eliminate high blood sugar factor of diabetes, the inventor of the present patent application has a first generation which had been issued for Taiwanese patent No. I453046 and U.S. Pat. No. 9,421,368. Although the first generation has fine effect, the inventor of the present patent application still puts into research for a perfect system. After long term conduction of extensive researches and experiments, the inventor finally completes a second generation of system as the present invention.

SUMMARY OF THE INVENTION

The primary objective of the present invention is to provide a system for relieving high blood sugar factor of diabetes. The system comprises an energy wave generator including a control unit and an output unit. The control unit includes an energy wave's frequency control mode for controlling and generating energy waves. The energy wave's frequency control mode is set up with multiple controls in multiple energy wave generation periods respectively. According to the multiple controls, the energy wave generator generates and emits energy waves in accordance with multiple base frequencies from 1 to 18150 Hz correspondingly to have corresponding multiple energy wave distribution densities with values from 0.99 to 7.25 for effecting on diabetic patients to relieve high blood sugar factor of diabetes. The energy wave distribution density (ED) is calculated by the following formula: $ED\text{-}\log_{10}(\text{freq.} \times D\% \times (2\text{Width}+1) \times (TT)+1)$, wherein freq., Width, D % and TT represent the base frequency, a predetermined sweep bandwidth, an emission rate and a total time of emission in a duty cycle of the base frequency respectively.

BRIEF DESCRIPTION OF THE DRAWINGS a

FIG. 4 is a schematic view of list of relations between spectrums of effect frequencies, modulation parameters and energy densities of the present invention;

DETAILED DESCRIPTION OF THE PREFERRED EMBODIMENT

Figure 1:
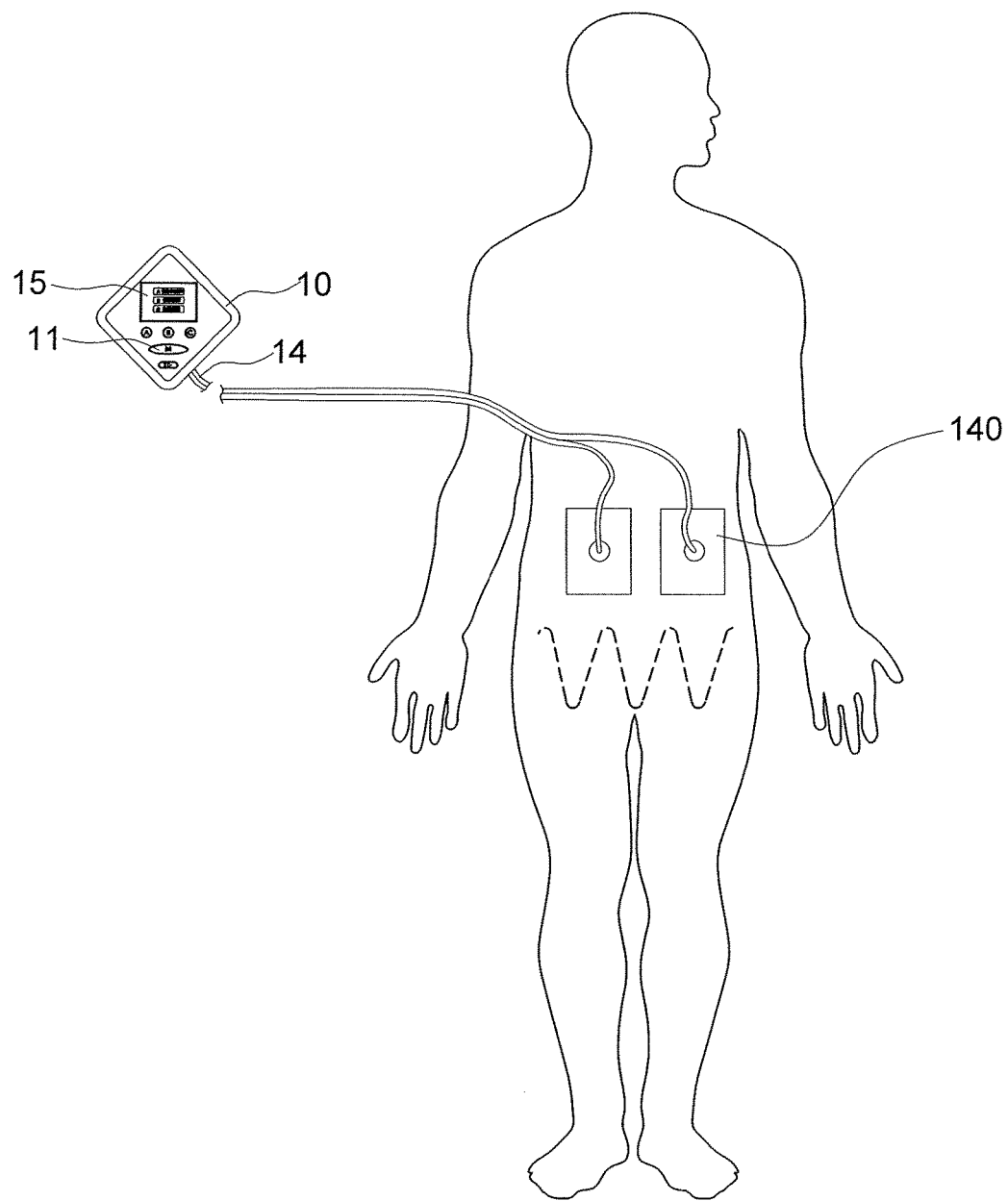
FIG. 1 is a schematic view of the system of the present invention.
Figure 2:
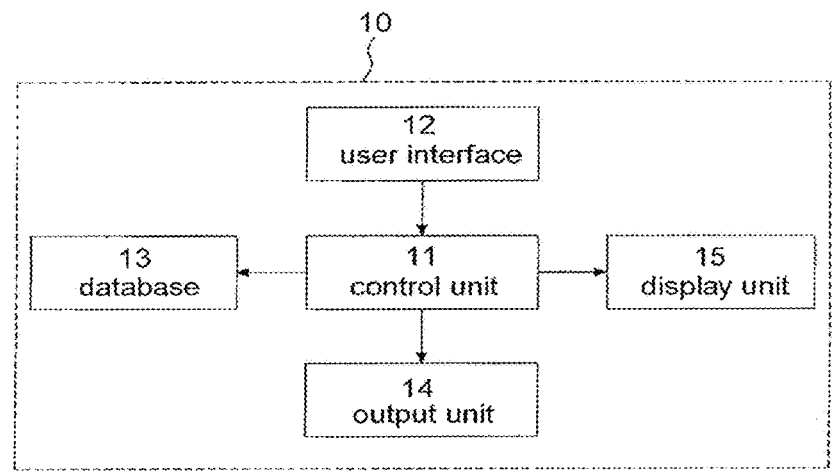
FIG. 2 is a schematic block diagram of units of the system of the present invention.

Referring to FIGS. 1 to 6, the system of the present invention comprises an energy wave generator 10. The energy wave generator 10 is set up with an energy wave's frequency control mode which includes multiple controls. According to the multiple controls, the energy wave generator 10 generates and emits energy waves (i.e. resonant wave) having corresponding energy wave distribution densities (EDs) and in accordance with corresponding base frequencies for effecting on bodies of diabetic patients to reduce or eliminate high blood sugar factors of diabetes. Referring to FIGS. 1 to 2, the energy wave generator 10 comprises a user interface 12, a control unit 11, a database 13 for saving the information of spectrums of effect frequency and modulation parameters corresponding to each effect frequency used in each energy wave generation periods, an energy wave output unit 14 and a display unit 15. In one embodiment of the present invention, the energy waves are in electric forms, and the energy wave output unit 14 includes a set of electrode sheets 140 for affixing to the body of diabetic patient so as to construct a circulation loop between the body and the electrical energy wave output unit 14 to transmit electric energy waves to the body of diabetic patient. The control unit 11 (such as a combination of microcontroller and driving circuit) sequentially reads the information of spectrums and modulation parameters of effect frequencies in the database 13, and then drives the energy wave output unit 14 to sequentially emits electrical energy waves each with a respective energy wave distribution density (ED) and in accordance with a respective base frequency in each corresponding energy wave generation period.

The control unit 11 of the present invention can be triggered to read the associated information of spectrums and modulation parameters in the database 13 by the command signals generated from the user interface 12, and then generates driving signals to control the energy wave output unit 14 (such as weak pulse generating circuit, voltage≤10V, current≤5 mA) switching on and off according to the corresponding frequencies, so that the energy wave output unit 14 generates corresponding electric energy waves with corresponding energy densities in required distributions of values in the corresponding energy wave generation periods. The display unit 15 is used to display the status of operation or procession of the system. Further, the embodiment of the present invention, the energy wave output unit 14 is not to be limited to a weak pulse generating circuit, the energy wave output unit 14 also may be a light emitting device or an audio play device enabling the energy wave generator system 10 to emits energy waves in light form or audio form in required corresponding frequencies.

In one embodiment of the invention, the energy wave generator 10 according to 1st to 9th sets of controls of the energy wave's frequency control mode sequentially outputs the energy waves each in accordance with a corresponding base frequency and having a corresponding energy wave distribution density (ED) from 1st to 9th energy wave generation periods correspondingly. The 1st to 9th sets of controls of the energy wave's frequency control mode are sequentially and respectively for: (a) continuously and sequentially generating a 1st to a 4th energy waves correspondingly having a 1st to a 4th energy wave distribution densities (EDs) and in accordance with a 1st to a 4th base frequencies respectively in the 1st energy wave generation period, wherein, the 1st ED of the 1st energy wave is between 2.47~6.19 (preferably 4.95), the 2nd ED of the 2nd energy wave is between 2.51~6.28 (preferably 5.02), the 3rd ED of the 3rd energy wave is between 2.49~6.24 (preferably 4.99), and the 4th ED of the 4th energy wave is between 2.46~6.16 (preferably 4.92); (b) continuously and sequentially generating a 5th to a 11th energy waves correspondingly having a 5th to a 11th energy wave distribution densities (EDs) and in accordance with a 5th to a 11th base frequencies respectively in the 2nd energy wave generation period, wherein, the 5th ED is between 2.52~6.29 (preferably 5.03), the 6th ED is between 2.36~5.89 (preferably 4.71), the 7th ED is between 2.90~7.25 (preferably 5.80), the 8th ED is between 2.34~5.85 (preferably 4.68), the 9th ED is between 2.34~5.854 preferably 4.68), the 10th ED is between 2.31~5.78 (preferably 4.63), the 11th ED is between 2.28~5.70 (preferably 4.56); (c) continuously and sequentially generating a 12th to a 17th energy waves correspondingly having a 12th to a 17th energy wave distribution densities (EDs) and in accordance with a 12th to a 17th base frequencies respectively in the 3rd energy wave generation period, wherein, the 12th ED is between 2.23~5.58 (preferably 4.46), the 13th ED is between 2.37~5.93 (preferably 4.75), the 14th ED is between 2.79~6.98 (preferably 5.58), the 15th ED is between 2.89~7.21 (preferably 5.77), the 16th ED is between 2.21~5.51 (preferably 4.41), the 17th ED is between 2.77~6.92 (preferably 5.54); (d) continuously and sequentially generating an 18th to a 23rd energy waves correspondingly having an 18th to a 23rd energy wave distribution densities (EDs) and in accordance with an 18th to a 23rd base frequencies respectively in the 4th energy wave generation period, wherein, the 18th ED is between 2.17~5.42 (preferably 4.34), the 19th ED is between 2.576.41 (preferably 5.13), the 20th ED is between 2.81~7.02 (preferably 5.61), the 21st ED is between 2.14~5.36 (preferably 4.29), the 22nd ED is between 2.48~6.21 (preferably 4.97), the 23rd ED is between 2.43~6.07 (preferably 4.86); (e) continuously and sequentially generating a 24th to a 28th energy waves correspondingly having a 24th to a 28th energy wave distribution densities (EDs) and in accordance with a 24th to a 28th base frequencies respectively in the 5th energy wave generation period, wherein, the 24th ED is between 2.29~5.73 (preferably 4.58), the 25th ED is between 2.18~5.46 (preferably 4.37), the 26th ED is between 2.46~6.15 (preferably 4.92), the 27th ED is between 1.90~4.75 (preferably 3.80), the 28th ED is between 1.85~4.63 (preferably 3.70); (f) continuously and sequentially generating a 29th to a 33rd energy waves correspondingly having a 29th to a 33rd energy wave distribution densities (EDs) and in accordance with, 29th to a 33rd base frequencies respectively in the 6th energy wave generation period, wherein, the 29th ED is between 2.08~5.20 (preferably 4.16), the 30th ED is between 1.41~3.53 (preferably 2.83), the 31st ED is between 1.33~3.33 (preferably 2.67), the 32nd ED is between 0.99~2.47 (preferably 1.97), the 33rd ED is between 2.05~5.13 (preferably 4.10); (g) continuously and sequentially generating a 34th to a 35th energy waves correspondingly having a 34th to a 35th energy wave distribution densities (EDs) and in accordance with a 34th to a 35th base frequencies respectively in the 7th energy wave generation period, wherein, the 34th ED is between 1.45~3.62 (preferably 2.90), the 35th ED is between 1.39~3.48 (preferably 2.78); (h) continuously and sequentially generating a 36th to a 37th energy waves correspondingly having a 36th to a 37th energy wave distribution densities (EDs) and in accordance with a 36th to a 37th base frequencies respectively in the 8th energy wave generation period, wherein, the 36th ED is between 1.39~3.48 (preferably 2.78), the 37th ED is between 1.45~3.62 (preferably 2.90); and (i) continuously and sequentially generating a 38th to a 39th energy waves correspondingly having a 38th to a 39th energy wave distribution densities (EDs) and in accordance with a 38th to a 39th base frequencies respectively in the 9th energy wave generation period, wherein, the 38th ED is between 1.79~4.48 (preferably 3.59), and the 39th ED is between 1.41~3.52 (preferably 2.82).

The value of aforementioned energy wave distribution densities (EDs) of the energy waves in accordance with their corresponding base frequencies are calculated by the formula: $ED = \log_{10}(\text{base freq.} \times D\% \times (2\text{Width}+1) \times (TT)+1)$. For example of the 1st base frequency in the 1st energy wave generation period, if we set the 1 st base freq.=18122 Hz, the emission rate in a duty cycle (D %)=70%, the predetermined sweep bandwidth (Width)=0 Hz and the total time of emission (TT)=7 secs in a duty cycle; and then the energy wave distribution density $(ED) = \log_{10}(18122 \times 70\% \times (2 \times 0+1) \times 7+1) = 4.95$. Although there is no specific unit referring to the energy wave distribution density (ED) of the present invention, the real meaning of ED represents a total transmit power of energy wave. When the frequency is higher, the times of switch voltage (current) is more, and energy used is more. The total time of emission means the duration of effect energy wave. The value of ED has been taken into account with all transmission parameters, which is on behalf of transmitting behavior. If each parameter is changed too large, the ED will also change. If the energy wave distribution density exceeds the scope of the set ones, the efficiency also will be changed with it.

Figure 3:
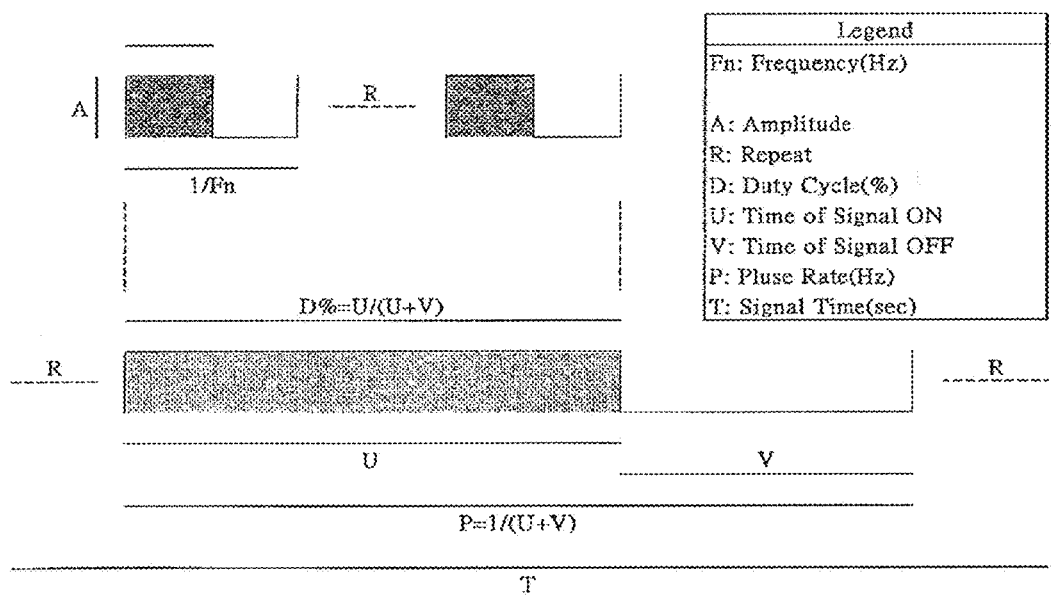
FIG. 3 is a schematic view of wave form of a duty cycle of the present invention.
Figure 4:
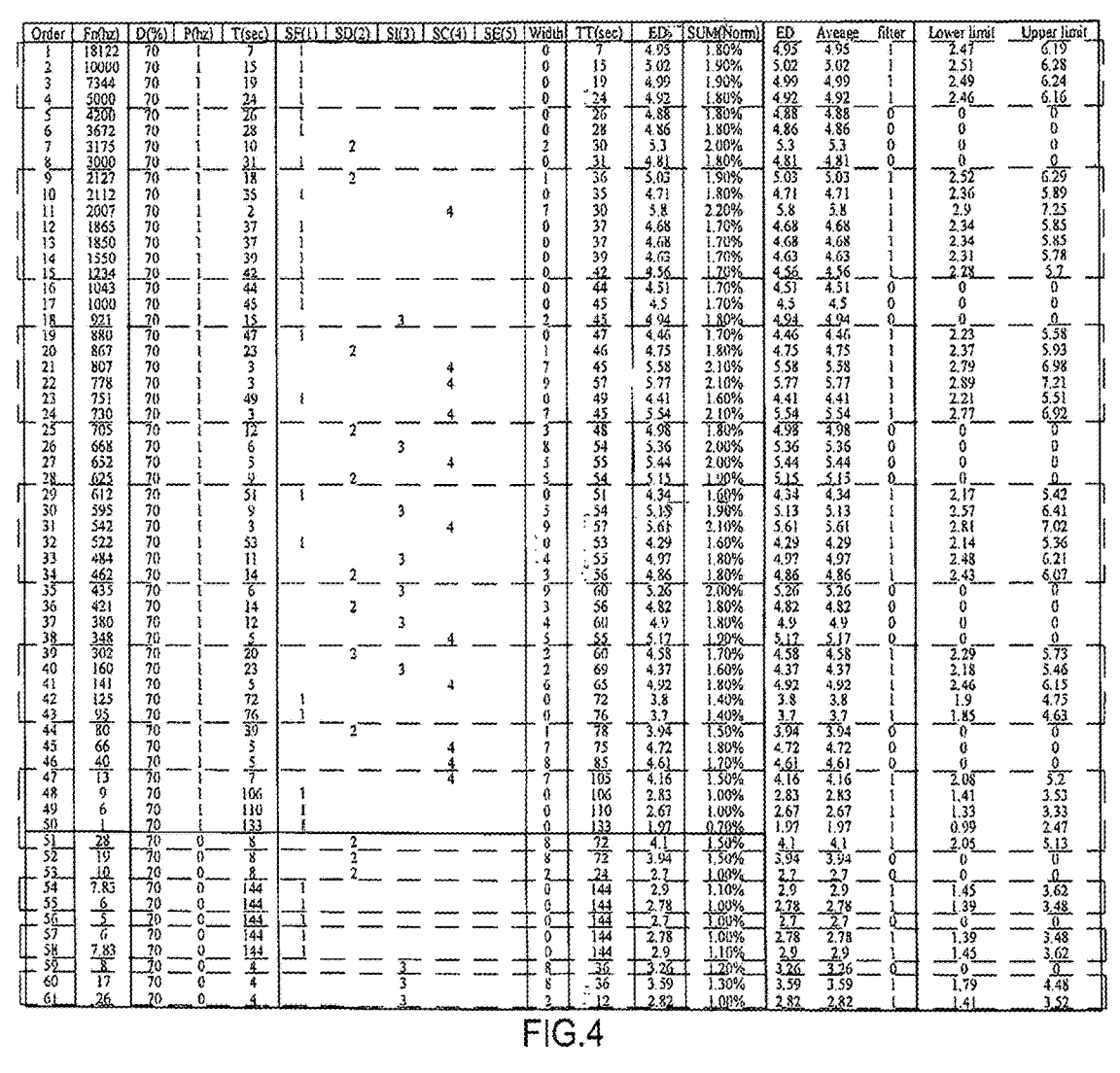

As shown in FIGS. 3 and 4, in one embodiment of the present invention, the energy wave is a square wave, D is the duty cycle, T is effect time of a single frequency, D % is emission rate of duty cycle of each base frequency and equal to U/(U+V). In the embodiment of present invention, we set the wave emission rate to be 70% for each duty cycle. U is the part of 70% which represents the time of signal outputs of positive potential in square wave, and V is the part of 30% which represents the time of signal outputs of 0 potential in OFF status. P represents a Pulse Rate (Hz) of frequency, P=1/(U+V). TT is the total time of emission period based on each base frequency in each duty cycle. In FIG. 4, the normalized percentages (normal) in each order, is the ratio between the ED in the effect period based on each base frequency and the sum of ED of the whole effect periods based on whole base frequencies from order 1 to 61 shown in FIG. 4.

Referring to FIG. 4, during the 1st energy wave generation period, the control mode of the 1st frequency is a fixed frequency sweep mode, which sets a fixed 1st base frequency within 18100~18150 Hz (preferable 18122 Hz), emission rate (D %)=70% for a duty cycle, sweep bandwidth (Width)=0 Hz and total time of emission (TT)=7 seconds for a duty cycle; the control mode of the 2nd base frequency is a fixed frequency sweep mode, which sets a fixed 2nd base frequency within 9900~10100 Hz (preferable 10000 Hz), D %=70%, Width=0 Hz and TT=15 secs for a duty cycle; the control mode of the 3rd base frequency is a fixed frequency sweep mode, which sets a fixed 3rd base frequency within 7300~7400 Hz (preferable 7344 Hz), D %=70%, Width=0 Hz and TT=19 secs for a duty cycle; and the control mode of the 4th base frequency is a fixed frequency sweep mode, which sets a fixed 4th base frequency within 4900~5100 Hz (preferable 5000 Hz), D %=70%, Width=0 Hz and TT=24 secs for a duty cycle.

Referring to FIG. 4, during the 2nd energy wave generation period, the control mode of the 5th base frequency is a sweep decreasing mode, which sets effect frequencies decreasingly adjusted based on a 5th base frequency between 2100~2150 Hz (preferable 2127 Hz) with D %=70%, Width=1 Hz, adjusted bandwidth equal to 1 Hz, and TT=36 seconds for a duty cycle; the control mode of the 6th base frequency is a fixed frequency sweep mode, which sets a fixed 6th base frequency between 2100~2130 Hz (preferable 2112 Hz) with D %=70%, Width=0 Hz and TT=35 secs for a duty cycle. The control mode of the 7th base frequency is a spread contract mode, which sets effect frequencies decreasing and increasing alternately adjusted to contract based on a 7th base frequency between 2000~2015 Hz (preferable 2007 Hz) with emission rate D %=70%, Width=7 Hz, adjusted bandwidth equal to 1 Hz and TT=30 seconds; the control mode of the 8th base frequency is a fixed frequency sweep mode, which sets a fixed 8th base frequency between 1860~1880 Hz (preferable 1865 Hz) with D %=70%, Width=0 Hz and TT=37 secs for a duty cycle; the control mode of the 9th base frequency is a fixed frequency sweep mode, which sets a fixed 9th base frequency between 1845~1855 Hz (preferable 1850 Hz) with D %=70%, Width=0 Hz and TT=37 secs for a duty cycle; the control mode of the 10th base frequency is a fixed frequency sweep mode, which sets a fixed 10th base frequency between 1540~1560 Hz (preferable 1550 Hz) with D %=70%, Width=0 Hz and TT=39 secs for a duty cycle; and the control mode of the 11th base frequency is a fixed frequency sweep mode, which sets a fixed 11th base frequency between 1230~1245 Hz (preferable 1234 Hz) with D %=70%, Width=0 Hz and TT=42 secs for a duty cycle.

Referring to FIG. 4, during the 3rd energy wave generation period, the control mode of the 12th base frequency is a fixed frequency sweep mode, which sets a fixed 12th base frequency between 870~890 Hz (preferable 880 Hz) with D %=70%, Width=0 Hz and TT=47 secs for a duty cycle; the control mode of the 13th base frequency is a sweep decreasing mode, which sets effect frequencies decreasingly adjusted based on a 13th base frequency between 860~880 Hz (preferable 867 Hz) with emission rate D %=70%, Width=1 Hz, adjusted bandwidth equal to 1 Hz, and TT=46 seconds for a duty cycle; the control mode of the 14th base frequency is a spread contract mode, effect frequencies decreasing and increasing alternately adjusted to contract based on a 14th base frequency between 800~820 Hz (preferable 807 Hz) with D %=70%, Width=7 Hz, adjusted bandwidth=1 Hz and TT=45 secs for a duty cycle; the control mode of the 15th base frequency is a spread contract mode, which sets effect frequencies decreasing and increasing alternately adjusted to contract based on a 15th base frequency between 770~785 Hz (preferable 778 Hz) with D %=70%, Width=9 Hz, adjusted bandwidth=1 Hz and TT=57 secs for a duty cycle; the control mode of the 16th base frequency is a fixed frequency sweep mode, which sets a fixed 16th base frequency between 745~765 Hz (preferable 751 Hz) with D %=70%, Width=0 Hz and TT=49 secs for a duty cycle; and the control mode of the 17th base frequency is a spread contract mode, which sets effect frequencies decreasing and increasing alternately adjusted to contract based on a 17th base frequency between 720~740 Hz (preferable 730 Hz) with D %=70%, Width=7 Hz, adjusted bandwidth=1 Hz and TT=45 secs for a duty cycle.

Referring to FIG. 4, during the 4th energy wave generation period, the control mode of the 18th base frequency is a fixed frequency sweep mode, which sets a fixed 18th base frequency between 605~620 Hz (preferable 612 Hz) with D %=70%, Width=0 Hz and TT=51 secs for a duty cycle; the control mode of the 19th base frequency is a sweep increasing mode, which sets effect frequencies increasingly adjusted based on a 19th base frequency between 590~610 Hz (preferable 595 Hz) with D %=70%, Width=5 Hz, adjusted bandwidth=1 Hz and TT=54 secs for a duty cycle; the control mode of the 20th base frequency is a spread contract mode, which sets effect frequencies decreasing and increasing alternately adjusted to contract based on a 20th base frequency between 535~560 Hz (preferable 542 Hz) with D %=70%, Width=9 Hz, adjusted bandwidth=1 Hz and TT=57 secs for a duty cycle; the control mode of the 21st base frequency is a fixed frequency sweep mode, which sets a fixed 21st base frequency between 515~535 Hz (preferable 522 Hz) with D %=70%, Width=0 Hz and TT=53 secs for a duty cycle; the control mode of the 22nd base frequency is a sweep increasing mode, which sets effect frequencies increasingly adjusted based on a 22nd base frequency between 476~495 Hz (preferable 484 Hz) with D %=70%, Width=4 Hz, adjusted bandwidth=1 Hz and TT=55 secs for a duty cycle; the control mode of the 23rd base frequency is a sweep decreasing mode, which sets effect frequencies decreasingly adjusted based on a 23rd base frequency between 455~475 Hz (preferable 462 Hz) with D %-70%, Width=3 Hz, adjusted bandwidth=1 Hz and TT=56 secs for a duty cycle.

Referring to FIG. 4, during the 5th energy wave generation period, the control mode of the 24th base frequency is a sweep decreasing mode, which sets effect frequencies decreasingly adjusted based on a 24th base frequency between 295~310 Hz (preferable 302 Hz) with D %=70%, Width=2 Hz, adjusted bandwidth=1 Hz and TT=60 secs for a duty cycle; the control mode of the 25th base frequency is a sweep increasing mode, which sets effect frequencies increasingly adjusted based on a 25th base frequency between 155~170 Hz (preferable 160 Hz) with D %=70%, Width=2 Hz, adjusted bandwidth=1 Hz and TT=69 secs for a duty cycle; the control mode of the 26th base frequency is a spread contract mode, which sets effect frequencies decreasing and increasing alternately adjusted to contract based on a 26th base frequency between 135~150 Hz (preferable 141 Hz) with D %=70%, Width=6 Hz, adjusted bandwidth=1 Hz and TT=65 secs for a duty cycle; the control mode of the 27th base frequency is a fixed frequency sweep mode, which sets a fixed 27th base frequency between 120~135 Hz (preferable 125 Hz) with D %=70%, Width=0 Hz and TT=72 secs for a duty cycle; and the control mode of the 28th base frequency is a fixed frequency sweep mode, which sets a fixed 28th base frequency between 90~110 Hz (preferable 95 Hz) with D %=70%, Width=0 Hz and TT=76 secs for a duty cycle.

Referring to FIG. 4, during the 6th energy wave generation period, the control mode of the 29th base frequency is a spread contract mode, which sets effect frequencies decreasing and increasing alternately adjusted to contract based on a 29th base frequency between 10~20 Hz (preferable 13 Hz) with D %=70%, Width=7 Hz, adjusted bandwidth=1 Hz and TT=105 secs for a duty cycle; the control mode of the 30th base frequency is a fixed frequency sweep-mode, which sets a fixed 30th base frequency between 5~25 Hz (preferable 9 Hz) with D %=70%, Width=0 Hz and TT=106 secs for a duty cycle; the control mode of the 31st base frequency is a fixed frequency sweep mode, which sets a fixed 31st base frequency between 4~15 Hz (preferable 6 Hz) with D %=70%, Width=0 Hz and TT=110 secs for a duty cycle; the control mode of the 32nd base frequency is a fixed frequency sweep mode, which sets a fixed 32nd base frequency between 1~6 Hz (preferable 1 Hz) with D %=70%, Width=0 Hz and TT=133 secs for a duty cycle; and the control mode of the 33rd base frequency is a sweep decreasing mode, which sets effect frequencies decreasingly adjusted based on a 33rd base frequency between 25~45 Hz (preferable 28 Hz) with D %=70%, Width=8 Hz, adjusted bandwidth=1 Hz and TT=72 secs for a duty cycle.

Referring to FIG. 4, during the 7th energy wave generation period, the control mode of the 34th base frequency is a fixed frequency sweep mode, which sets a fixed 34th base frequency between 5~20 Hz (preferable 7.83 Hz) with D %=70%, Width=0 Hz and TT=144 secs for a duty cycle; and the control mode of the 35th base frequency is a fixed frequency sweep mode, which sets a fixed 35th base frequency between 5~15 Hz (preferable 6 Hz) with D %=70%, Width=0 Hz and TT=144 secs for a duty cycle.

Referring to FIG. 4, during the 8th energy wave generation period, the control mode of the 36th base frequency is a fixed frequency sweep mode, which sets a fixed 36th base frequency between 5~8 Hz (preferable 6 Hz) with D %=70%, Width=0 Hz and TT=144 secs for a duty cycle; and the control mode of the 37th base frequency is a fixed frequency sweep mode, which sets a fixed 37th base frequency between 6~15 Hz (preferable 7.83 Hz) with D %=70%, Width=0 Hz and TT=144 secs for a duty cycle.

Referring to FIG. 4, during the 9th energy wave generation period, the control mode of the 38th base frequency is a sweep increasing mode, which sets effect frequencies increasingly adjusted based on a 38th base frequency between 15~28 Hz (preferable 0.17 Hz) with D %=70%, Width=8 Hz, adjusted bandwidth=1 Hz and TT=36 secs for a duty cycle; and the control mode of the 39th base frequency is a sweep increasing mode, which sets effect frequencies increasingly adjusted based on a 39th base frequency between 24~35 Hz (preferable 26 Hz) with D %=70%, Width=2 Hz, adjusted bandwidth=Hz and TT=12 secs for a duty cycle.

The fixed frequency sweep mode depicted in the present invention means that the frequency of each treatment is functioning at a fixed frequency until the total time of the frequency effect period is end. In the case of the 1st energy wave generation period, for example, assuming that the first frequency is 18122 Hz, then the 1st base frequency is fixed at 18122 Hz until the total time of the frequency reaches 7 seconds. After that, it goes to the next frequency effect period, and so on. Because there is no value change of the frequency range for the fixed frequency sweep mode, therefore, the predetermined sweep bandwidth (Width) is 0 Hz.

Referring to FIG. 4, the control of the aforementioned sweep decreasing mode is to control the system to emit the energy wave by decreasing frequency distribution with an adjusted bandwidth in a predetermined sweep bandwidth. The calculation of the value change of the sweep decreasing mode depicted in the present invention is described as below. The first output frequency is calculated as a base frequency (Fn) plus a predetermined sweep bandwidth (Width), and the second output frequency is calculated as the first output frequency minus an adjusted bandwidth (such as 1 Hz). When the current output frequency is equal to the base frequency (Fn), the current output frequency will be the last output frequency. In the case of the fifth frequency (freq), for example, the base frequency is 2127.2 Hz with a predetermined sweep bandwidth (Width) of 1 Hz. Based on the above formula, two frequencies can be obtained, and the sequential output frequencies are 2128.2 Hz and 2127.2 Hz respectively. Each single-frequency's effect time (T) in the sweep decreasing mode is 18 seconds, so that the total time (TT) of the two effect frequencies is 36 seconds, i.e., TT=(m+1)*T, wherein, m=Width/adjusted bandwidth=1 Hz/1 Hz=1.

Referring to FIG. 4, the control of the aforementioned sweep increasing mode is to control the system to emit the energy wave by increasing frequency distribution with an adjusted bandwidth in a predetermined sweep bandwidth. The calculation of the value change of the sweep increasing mode depicted in the present invention is described as below. The first output frequency is calculated as a base frequency (Fn) minus a predetermined sweep bandwidth (Width), and the second output frequency is calculated as the first output frequency plus an adjusted bandwidth (such as 1 Hz). When the current output frequency is equal to the base frequency (Fn), the current output frequency will be the last output frequency. In the case of the nineteenth base frequency, for example, the base frequency is 603.4 Hz with a predetermined sweep bandwidth (Width) 5 Hz and adjusted bandwidth 1 Hz. Based on the above formula, six frequencies can be obtained, and the sequential output frequencies are 598.4 Hz, 599.4 Hz, 600.4 Hz, 601.4 Hz, 602.4 Hz and 603.4 Hz respectively. Each single-frequency's effect time (T) in the sweep increasing mode is 9 seconds, so that the total time of the six frequencies (TT) is 54 seconds, i.e., TT=(m+1)*T, wherein m=Width/adjusted bandwidth=5 Hz/1 Hz=5.

Referring to FIG. 4, the control of the aforementioned spread contract mode is to control the system to emit the energy wave by alternately increasing frequency and decreasing frequency distribution with an adjusted bandwidth in a predetermined sweep bandwidth. The calculation of the value change of the spread contract mode depicted in the present invention is described as below. The first output frequency is calculated as a base frequency (Fn) minus the predetermined sweep bandwidth (Width), the second output frequency is calculated as a base frequency (Fn) plus the predetermined sweep bandwidth (Width), the third output frequency is calculated as the first output frequency plus the adjusted bandwidth (such as 1 Hz), the fourth output frequency is calculated as the second output frequency minus the adjusted bandwidth (such as 1 Hz), and so on. When the current output frequency is equal to the base frequency (Fn), the current output frequency will be the last output frequency. In the case of the seventh frequency, for example, the base frequency is 2010.9 Hz with sweep bandwidth 7 Hz and adjusted bandwidth 1 Hz. Based on the above formula, fifteen frequencies can be obtained, and the sequential output frequencies are 2003.9 Hz, 2017.9 Hz, 2004.9 Hz, 2016.9 Hz, 2005.9 Hz, 2015.9 Hz, 2006.9 Hz, 2014.9 Hz, 2007.9 Hz, 2013.9 Hz, 2008.9 Hz, 2012.9 Hz, 2009.9 Hz, 2011.9 Hz and 2010.9 Hz respectively. Each single-frequency's treatment time (T) is 2 seconds, so that the total time of the fifteen frequencies (TT) is 30 seconds, i.e., TT=(2m+1)*T, wherein m=Width/adjusted bandwidth=7 Hz/1 Hz=7.

Figure 5:
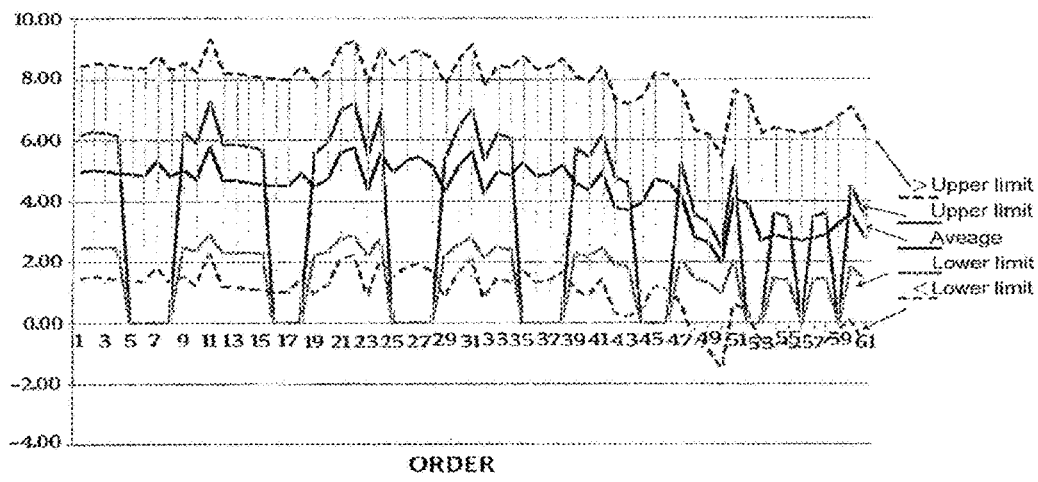
FIG. 5 is a schematic view of distribution of energy density on linear timeline of the present invention.
Figure 6:
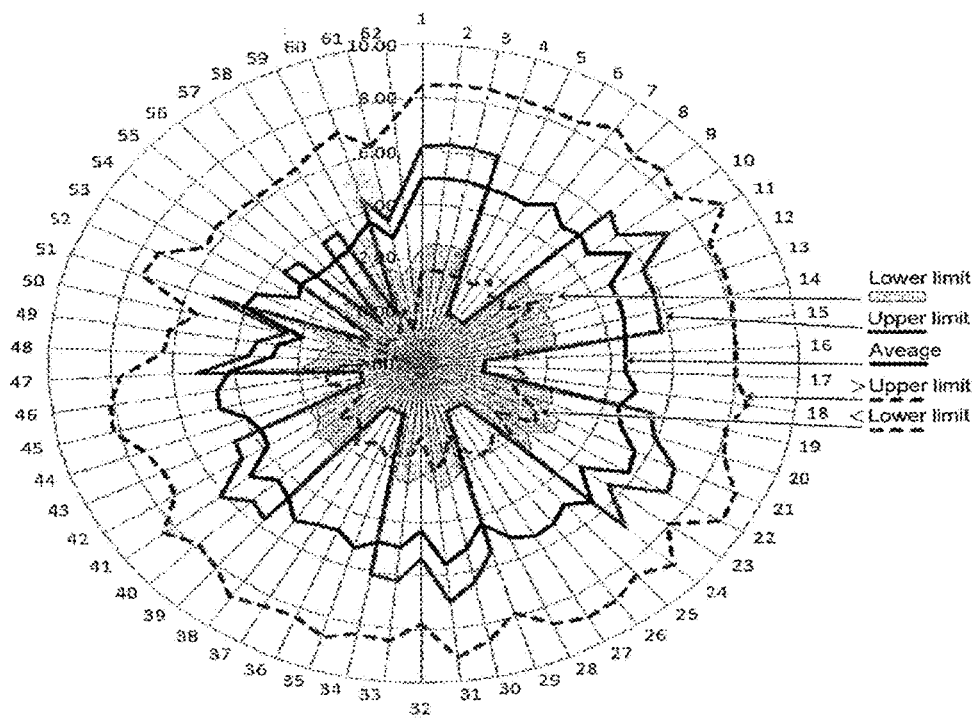
FIG. 6 is a schematic view of distribution of energy density on circular timeline of the present invention.

FIG. 5 shows the distribution schematic of the energy density in energy wave's frequency control mode against the linear timeline in the present invention. Wherein, the upper limit and the lower limit shown in FIG. 5 represent the upper range and the lower range of the energy density against the timeline mentioned above in accordance with the present invention. FIG. 6 shows the distribution schematic of the energy density in energy wave's frequency control mode against the annular timeline in the present invention. Wherein, the central portion is the average distribution of the energy density against the timeline mentioned above in accordance with the present invention.

On the chart shown in FIG. 4, the frequency distributions of first to ninth energy wave generation periods are from orders 1-4, 9-15, 19-24, 29-34, 39-43, 47-51, 54-55, 57-58 and 60-61 chronologically respectively.

In the present embodiment, besides above frequency treatment period, the energy wave's frequency control mode also includes eight non-energy periods, i.e., from the first to the eighth non-energy periods generated between every two adjacent energy density from the first to the ninth periods correspondingly. The total time of the first to eighth non-energy periods are 115, 134, 211, 231, 238, 96, 144 and 36 seconds respectively. The energy wave generator 10 generates various frequencies in each non-energy periods and filters the frequency to have non-energy. Referring to FIG. 4, the first to the eighth non-energy periods is chronologically generated in-between order 5-8, order 16-18, order 25-28, order 35-38, order 44-46, order 52-53, order 56 and order 59 in sequence.

Figure 7:
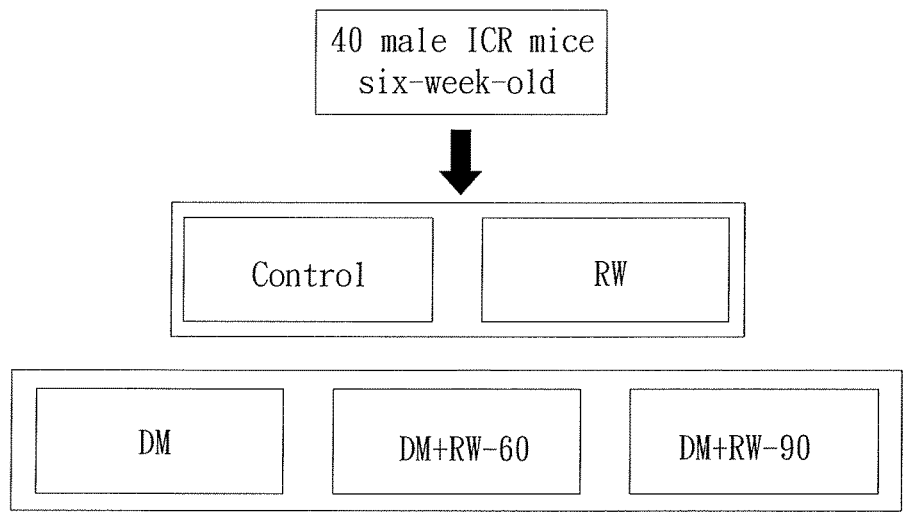
FIG. 7 is a schematic view of experimental process of the present invention. Fig.
Figure 8:
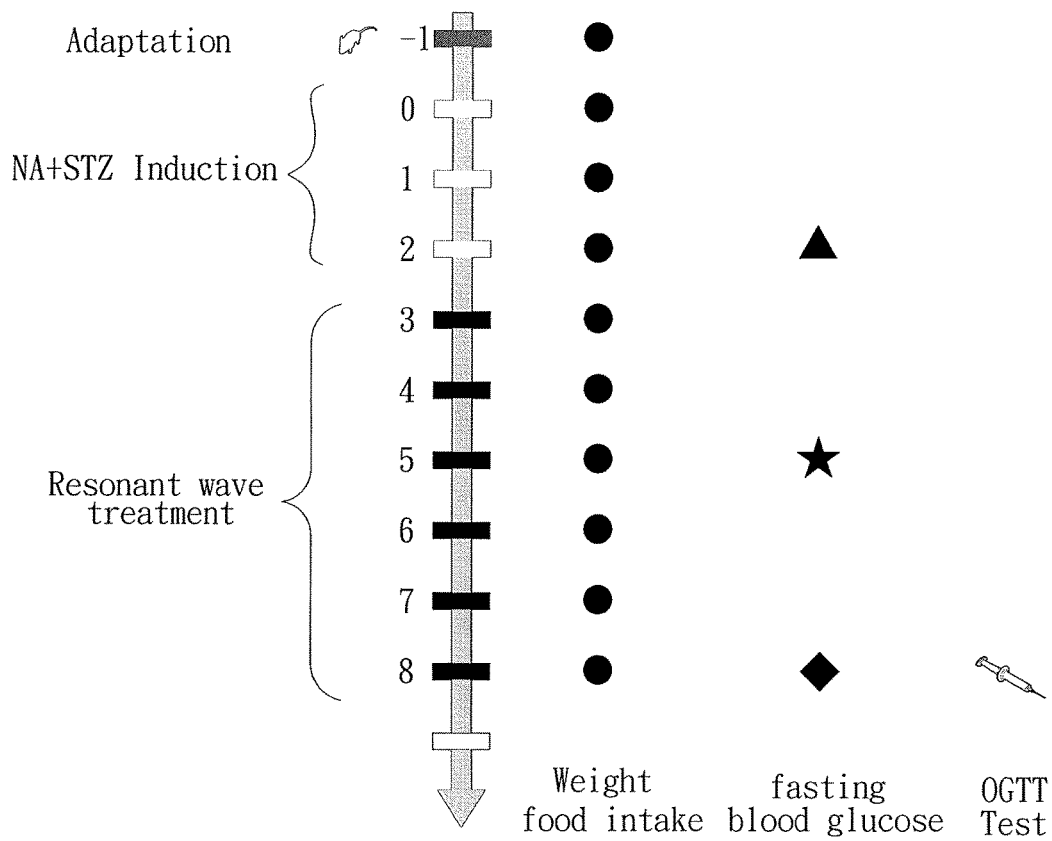
FIG. 8 is a schematic view of experimental structure with time course of the present invention.
Figure 9:
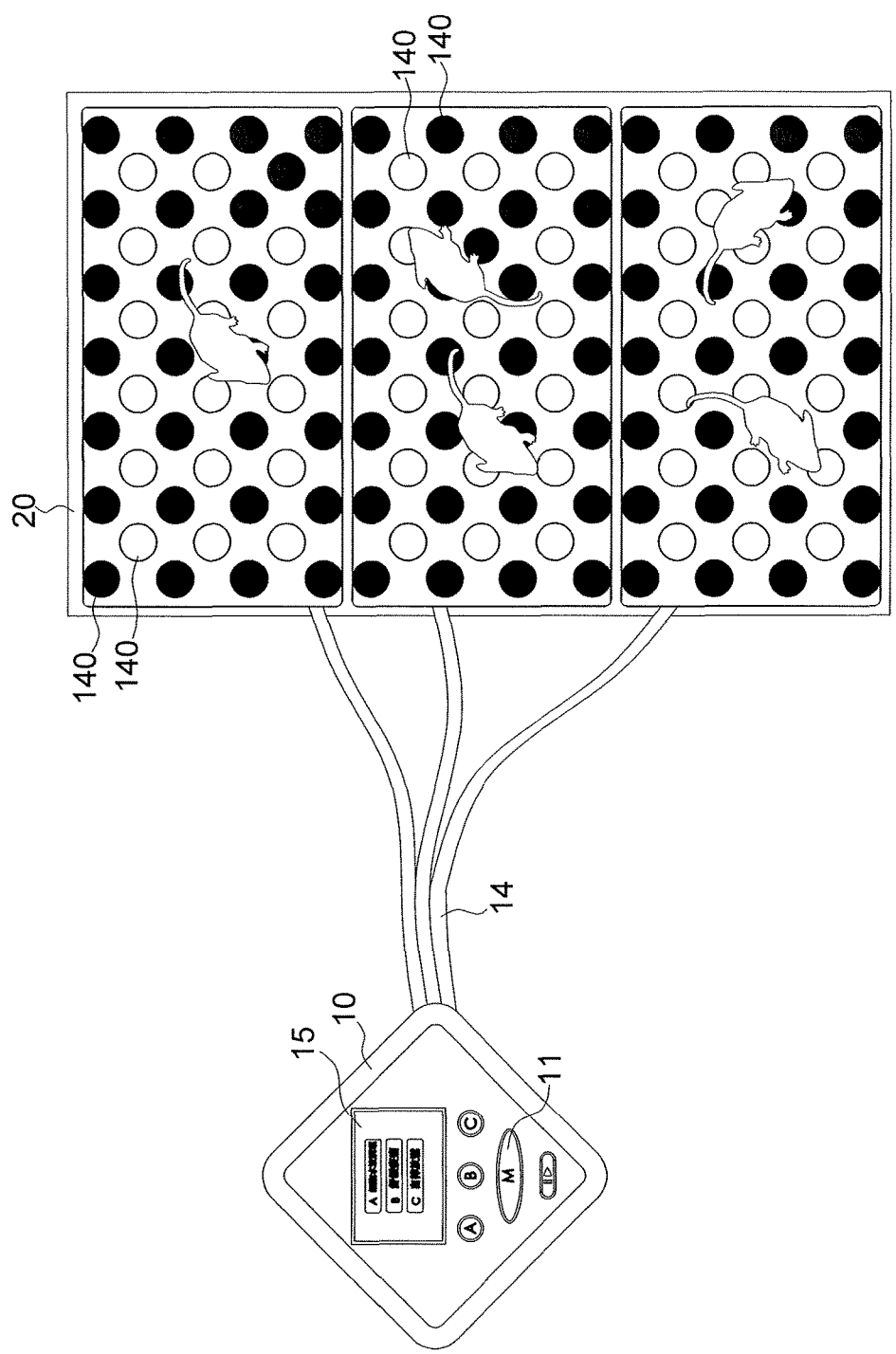
FIG. 9 is a schematic view of resonant wave treatment on mice by electrical stimulation floor of the present invention.

In order to verify the feasibility of the present invention, the inventor has carried out animal experiments as embodiments shown in FIGS. 7-9. First, referring to FIGS. 7-9, around 40 male ICR mice about six-week-old were prepared, and then the mice were divided into a normal group and a diabetic group. Wherein, the normal group was divided into a normal control group (Control group, healthy mice without resonant wave treatment) and a resonant wave control group (RW group, healthy mice with resonant wave treatment). The diabetic group was divided into a diabetic control group (DM group, diabetic mice without resonant wave treatment), a diabetic with 60 minutes resonant wave intervened group ((DM+RW-60) group, diabetic mice with one time resonant wave treatment), and a diabetic with 90 minutes resonant wave intervened group ((DM+RW-90) group, diabetic mice with 1.5 times resonant wave treatment). Referring to FIG. 8, the first week was an adaptation period for the mice, and the second week was an induction period (NA+STZ induced) for the mice to be applied nicotine amide (NA) and streptozotocin (STZ). The 3rd-8th weeks were the resonant wave treatment period for the mice to be placed on the base plate 20 with a plurality of electrode pads 140, which is linked to the resonant wave generator shown in FIG. 9. The resonant wave treatment period lasted 6 weeks, 5 times per week.

Figure 10A:
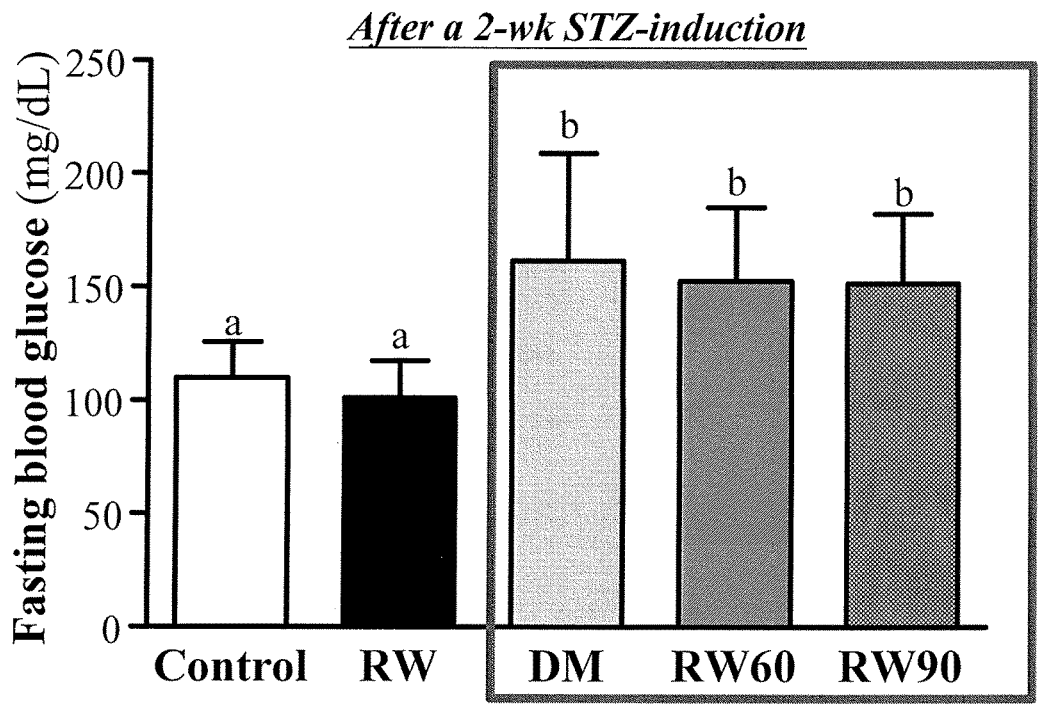
FIG. 10A is a schematic view of fasting blood glucose of healthy mice and mice after 2 weeks STZ-induction of the present invention.
Figure 10B:
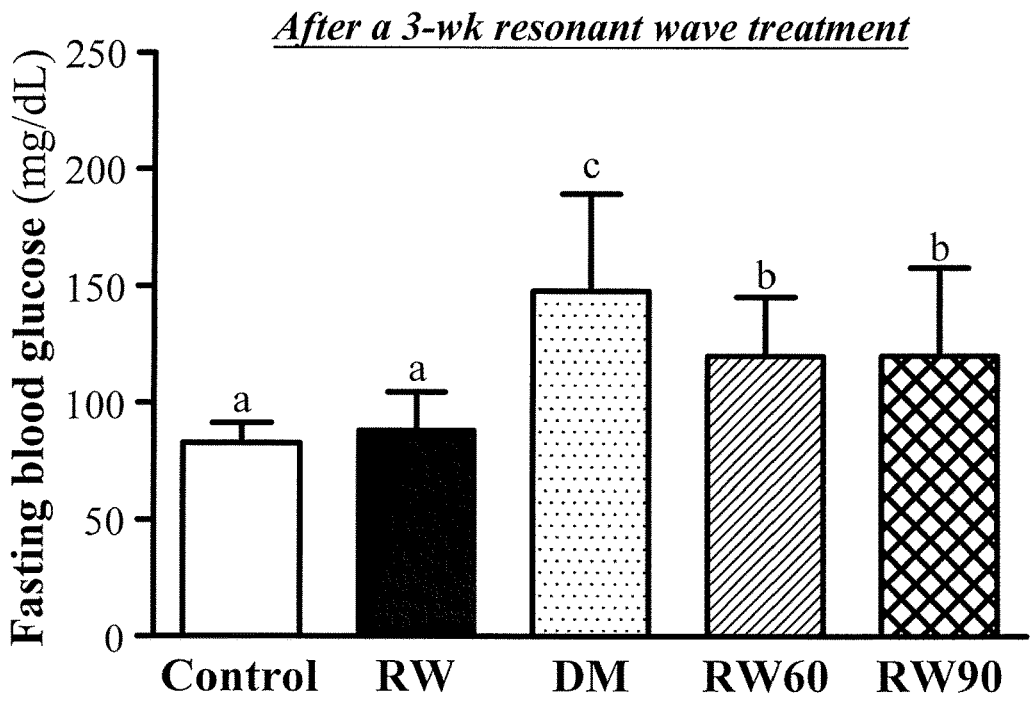
FIG. 10B is a schematic view of fasting blood glucose of mice after 3 weeks resonant wave treatment of the present invention.

FIG. 10A shows a schematic comparison of fasting blood glucose of the STZ-induced mice in each group after 2 weeks. FIG. 10B shows a schematic comparison of fasting blood glucose of the mice with resonant wave intervened in each group after 3 weeks. Wherein, as shown in FIG. 10A, the grouping data is based on the fasting blood glucose after STZ-induction, and the GLU-AC of the normal control group (Control), the resonant wave control group (RW), the diabetic control group (DM), the diabetic with 60 minutes resonant wave intervened group (RW60), and the diabetic with 90 minutes resonant wave intervened group (RW90) are 109.8±15.9, 101.1±16.3, 161.8±47.3, 152.8±32.2, and 151.7±30.7 (mg/dL) correspondingly. It shows that the diabetic initial GLU-AC of DM, RW60 and RW90 three STZ-induced groups reach the level of illness and are significantly higher than the Control group and the RW group ($P<0.001$). Therefore, resonant wave intervened experiments can be proceeded. After three weeks, shown in FIG. 10B, the GLU-AC of Control, RW, DM, RW60 and RW90 five groups are 82.8±8.5, 88.3±16.3, 148.1±41.4, 120.1±25.5, and 120.3±37.7 (mg/dL) correspondingly. It shows that the DM group is significantly 1.79 and 1.68 times higher than the Control group and the RW group ($P<0.0001$). After a resonant wave intervention, the RW60 and RW90 groups are significantly reduced 18.9% ($P=0.0117$) and 18.8% ($P=0.0138$) respectively in comparison with the DM group. As a result, the RW60 and RW90 groups have significant effect to lower diabetic fasting blood glucose.

Figure 11:
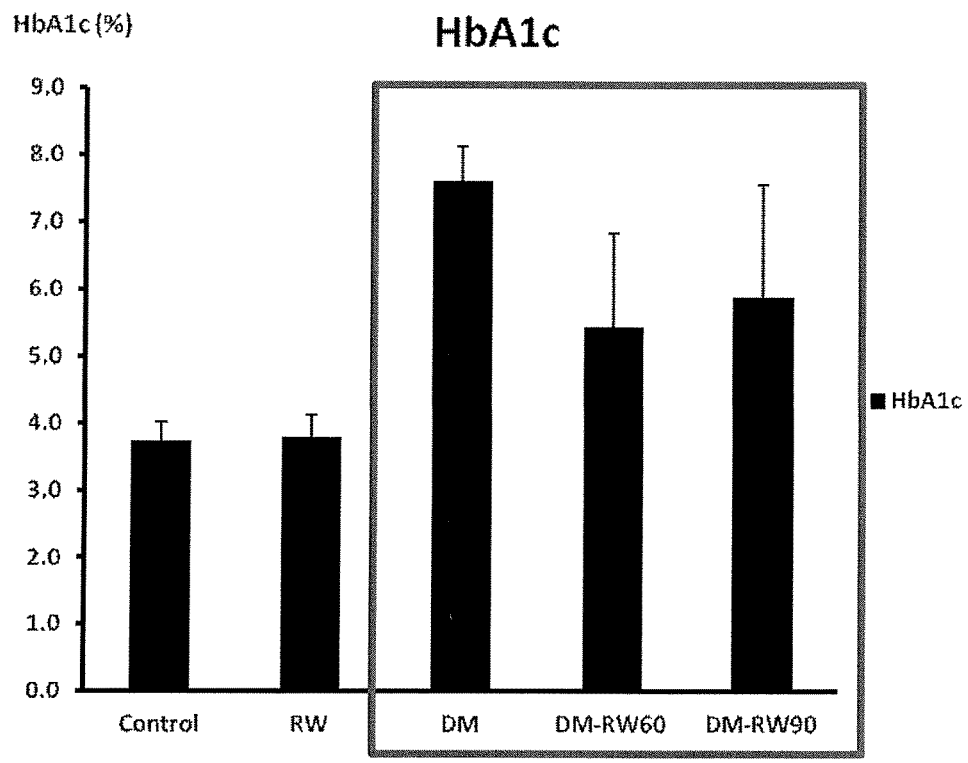
FIG. 11 is a schematic view of comparison of glycated hemoglobin of mice after 8 weeks resonant wave treatment of the present invention.
Figure 12:
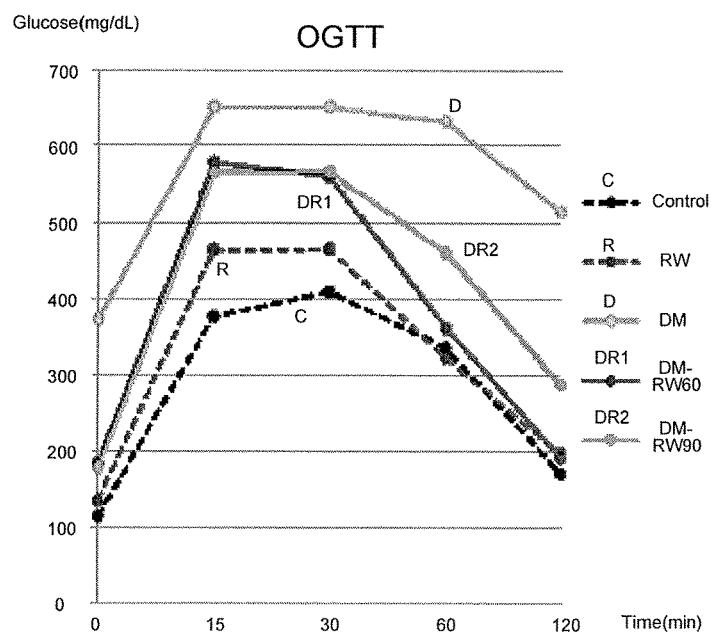
FIG. 12 is a schematic view of time line chart without SD based blood glucose analysis of mice after 8 weeks resonant wave treatment of the present invention.
Figure 13:
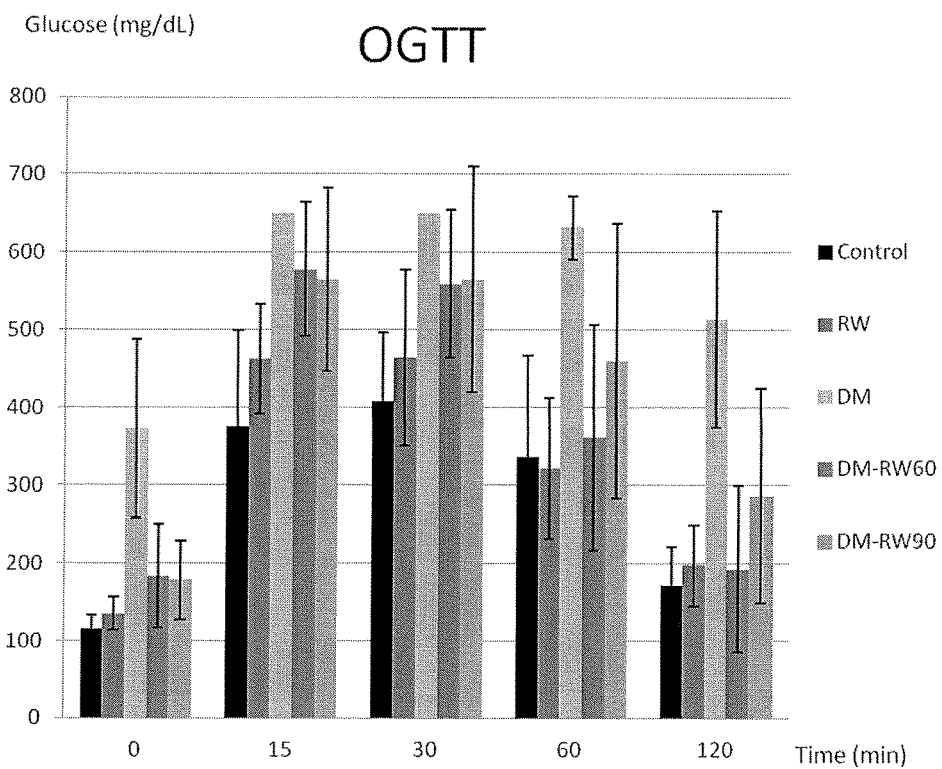
FIG. 13 is a schematic view of time bar graph with SD based blood glucose analysis of mice after 8 weeks resonant wave treatment of the present invention.
Figure 14:
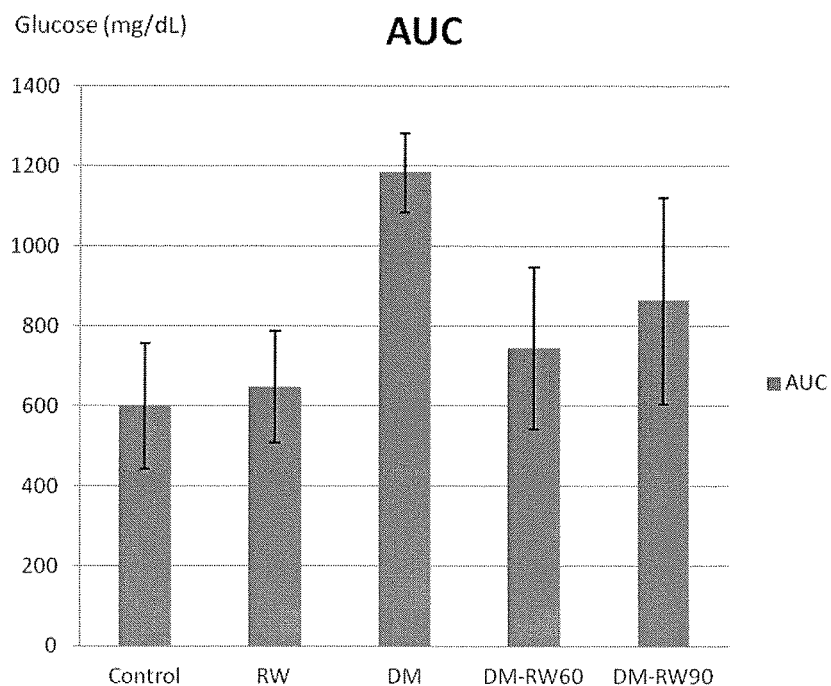
FIG. 14 is a schematic view of area under response curve of the blood glucose within 2 hours after 8 weeks resonant wave treatment of the present invention.
Figure 15:
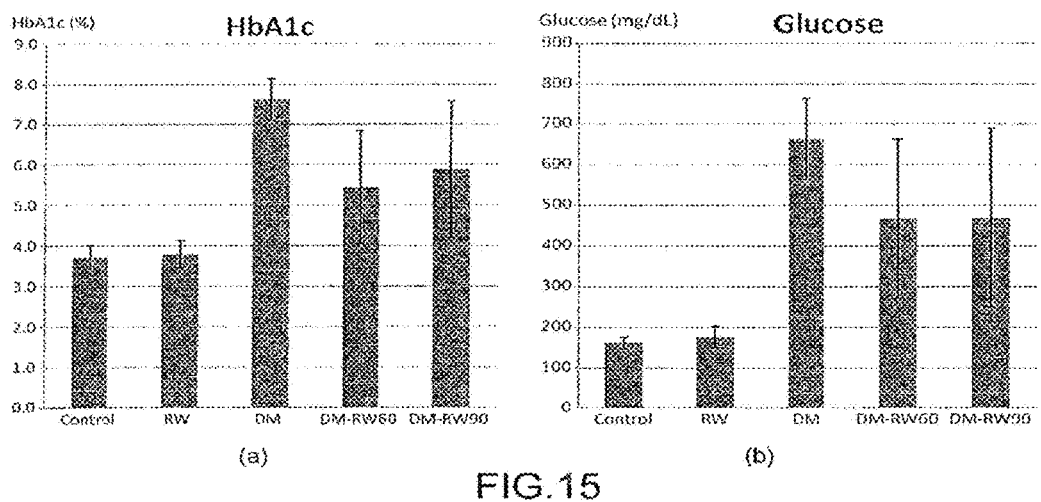
FIG. 15 is a schematic view of the comparison of glycated hemoglobin HbA1c (shown as Fig. (a)) and the comparison of glucose (shown as Fig. (b)) after 8 weeks resonant wave treatment of the present invention.
Figure 16:
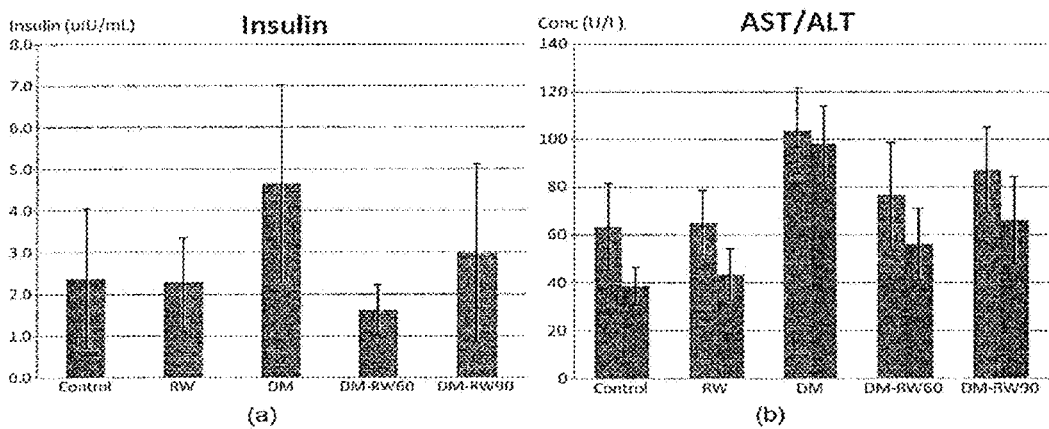
FIG. 16 is a schematic view of insulin (shown as Fig. (a)) and indicators AST (SGOT) for liver, heart, skeletal muscle cells inflammatory and specificity indicators ALT(SGPT) for liver inflammation (shown as Fig. (b)) by the blood analysis after 8 weeks resonant wave treatment of the present invention.
Figure 17:
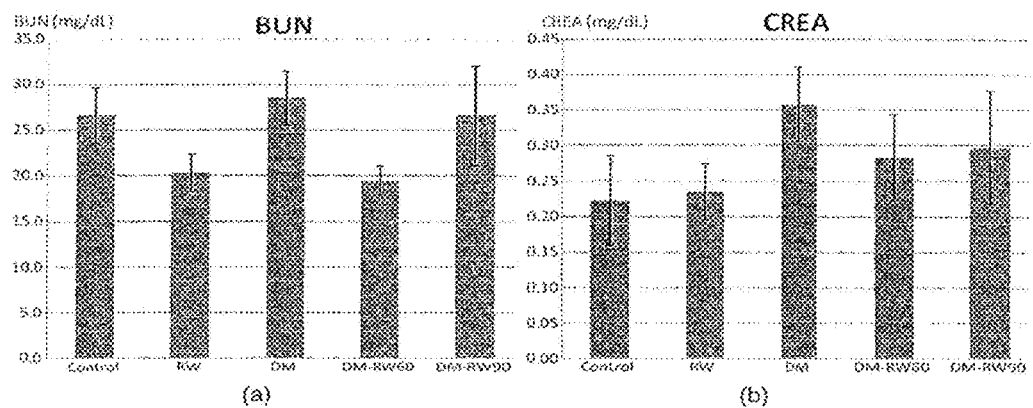
FIG. 17 is a schematic view of BUN (shown as Fig. (a)) and CREA (shown as Fig. (b)) by the blood analysis after 8 weeks resonant wave treatment of the present invention.

FIG. 11 shows a schematic comparison of glycated hemoglobin of the mice with resonant wave intervened in each group after 8 weeks. Wherein, the grouping data is based on the fasting blood glucose after STZ-induction, and the GLU-AC of the normal control group (Control), the resonant wave control group (RW), the diabetic control group (DM), the diabetic with 60 minutes resonant wave intervened group (DM-RW60), and the diabetic with 90 minutes resonant wave intervened group (DM-RW90) are 3.7±0.3, 3.8±0.3, 7.6±0.5, 5.4±1.4, and 5.9±1.7(%) correspondingly. FIGS. 12-17 show the blood analyses of the mice with resonant wave intervened in each group after 8 weeks. Each item from the main data of the blood analyses shows that the diabetic with 60 minutes resonant wave intervened group (DM-RW60) and the diabetic with 90 minutes resonant wave intervened group (DM-RW90) both tend to be better than the diabetic control group (DM).

Figure 18:
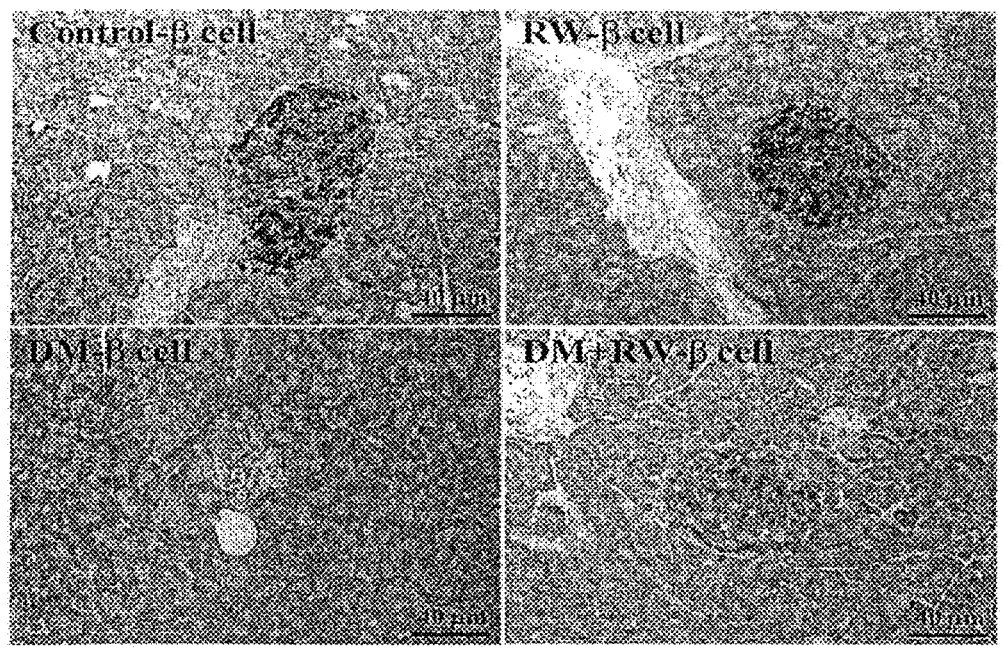
FIG. 18 is a schematic view of pancreas specimen of the two groups of mice by insulin antibody immunohistochemistry of the present invention.
Figure 19:
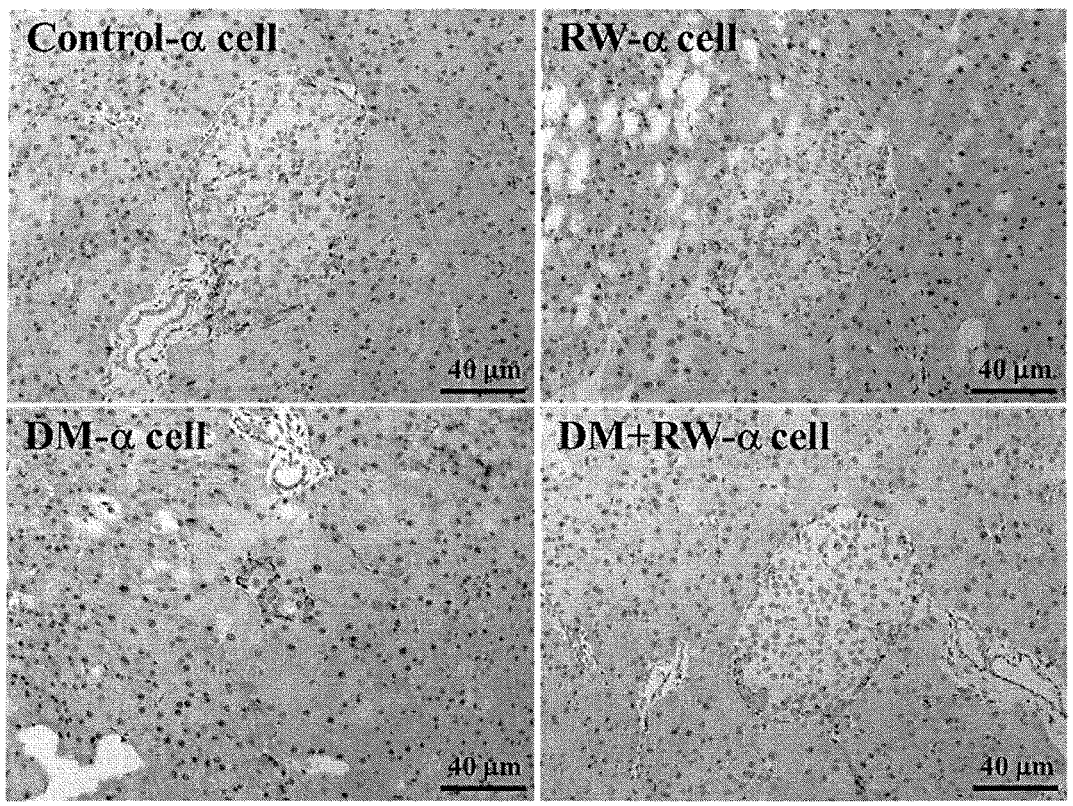
FIG. 19 is a schematic view of pancreas specimen of the two groups of mice by anti-glucagon antibody immunohistochemistry of the present invention.

Referring to FIG. 18, the immunohistochemistry staining results from anti-insulin antibody shows that animal's pancreatic specimens from the Control and the RW groups can be observed that the islet tissue is full of normal insulin secretion β cells (cytoplasm showing brown positive reaction) and its staining shows strong positive. Islet tissues from the DM group can be observed that only a very small amount of weak positive β cells scattered in atrophied islets. Conversely, pancreatic tissues from the DM+RW groups show that the β cell amounts and staining are significantly more than the DM group. Referring to FIG. 19 again, the immunohistochemistry staining results from anti-glucagon antibody shows that only a small amount of α cells with glucagon staining positive scattered in islet tissues but positive α cell amounts and staining in each Control, RW, DM and DM+RW group has no significant differences and are significantly better than the DM group.

While we have shown and described the embodiment in accordance with the present invention, it should be clear to those skilled in the art that further embodiments may be made without departing from the scope of the present invention.

What is claimed is:

1. A system for relieving high blood sugar factor of diabetes, comprising an energy wave generator, the energy wave generator including a control unit and an output unit, the control unit including an energy wave's frequency control mode configured to control and generate energy waves, the energy wave's frequency control mode including multiple controls which operate in multiple energy wave generation periods respectively; according to the multiple controls of the control unit, the energy wave generator configured to generate energy waves in accordance with multiple base frequencies and having multiple energy wave distribution densities (EDs) correspondingly; the energy waves configured to be emitted out by electrode sheets of the output unit configured to effect bodies of diabetic patients to reduce or eliminate high blood sugar factors of diabetes; the energy wave's frequency control mode comprising at least one fixed frequency sweep mode, at least one sweep decreasing mode, at least one spread contract mode and/or at least one sweep increasing mode; the energy wave generator configured to emit energy waves configured to have a decreasing frequency distribution in a predetermined sweep bandwidth by a predetermined adjusted bandwidth in the at least one sweep decreasing mode, to have an increasing frequency distribution in a predetermined sweep bandwidth by a predetermined adjusted bandwidth in the at least one sweep increasing mode, and to have an increasing frequency distribution and a decreasing frequency distribution alternately in a predetermined sweep bandwidth by a predetermined adjusted bandwidth in the at least one spread contract mode; the energy wave distribution density (ED) being calculated by the following formula: ED=log$_{10}$ (freq.×D%×(2Width+1)×(TT)+1), wherein freq., Width, D % and TT represent the base frequency, the predetermined sweep bandwidth, an emission rate and a total time of emission in a duty cycle of the base frequency respectively, wherein, the multiple controls configured to be at least two sets of controls selected from the group consisting of a 1st, a 2nd, a 3rd, a 4th, a 5th, a 6th, a 7th, an 8th and a 9th sets of controls; wherein according to the 1 st, 2nd, 3rd, 4th, 5th, 6th, 7th, 8th and 9th sets of controls, the energy wave generator in a 1st, a 2nd, a 3rd, a 4th, a 5th, a 6th, a 7th, an 8th and a 9th energy wave generation periods configured to generate a 1st, a 2nd, a 3rd, a 4th, a 5th, a 6th, a 7th, a 8th and a 9th sets of energy waves in accordance with a 1st, a 2nd, a 3rd, a 4th, a 5th, a 6th, a 7th, an 8th and a 9th sets of base frequencies of 4900~18150 Hz, 1230~2130 Hz, 720~890 Hz, 455~620 Hz, 90~310 Hz, 1~45 Hz, 5~20 Hz, 5~15 Hz and 15~35 Hz correspondingly and having a 1st, a 2nd, a 3rd, a 4th, a 5th, a 6th, a 7th, an 8th and a 9th sets of EDs of 2.46~6.28, 2.28~7.25, 2.21~7.21, 2.14~7.02, 1.85~6.15, 0.99~5.20, 1.39~3.62, 1.39~3.62 and 1.41~4.48 correspondingly; and wherein the base frequencies of the at least two sets of controls are sequentially lower one by one.

2. The system for relieving high blood sugar factor of diabetes as claimed in claim 1, wherein there is a non-energy period between every two adjacent periods of the multiple energy wave generation periods.

3. The system for relieving high blood sugar factor of diabetes as claimed in claim 2, wherein the total time of the non-energy period is selected from the group consisting of 115, 134, 211, 231, 238, 96, 144 and 36 seconds.

4. The system for relieving high blood sugar factor of diabetes as claimed in claim 1, wherein in the 1st energy wave generation period corresponding to the 1st set of controls, the 1st set of energy waves are sequentially a 1st to a 4th energy waves correspondingly with a 1st to a 4th EDs and in accordance with a 1st to a 4th base frequencies respectively, the 1st ED is 2.47~6.19 and the 1st base frequency is 18100~18150 Hz, the 2nd ED is 2.51~6.28 and the 2nd base frequency is 9900~10100 Hz, the 3rd ED is 2.49~6.24 and the 3rd base frequency is 7300~7400 Hz, and the 4th ED is 2.46~6.16 and the 4th base frequency is 4900~5100 Hz; in the 2nd energy wave generation period corresponding to the 2nd set of controls, the 2nd set of energy waves are sequentially a 5th to a 11th energy waves correspondingly with a 5th to a 11th EDs and in accordance with a 5th to a 11th base frequencies respectively, the 5th ED is 2.52~6.29 and the 6th base frequency is 2100~2150 Hz, the 6th ED is 2.36~5.89 and the 6th base frequency is 2100~2130 Hz, the 7th ED is 2.90~7.25 and the 7th base frequency is 2000~2015 Hz, the 8th ED is 2.34~5.85 and the 8th base frequency is 1860~1880 Hz, the 9th ED is 2.34~5.85 and the 9th base frequency is 1845~1855 Hz, the 10th ED is 2.31~5.78 and the 10th base frequency is 1540~1560 Hz, the 11th ED is 2.28~5.70 and the 11th base frequency is 1230~1245 Hz; in the 3rd energy wave generation period corresponding to the 3rd set of controls, the 3rd set of energy waves are sequentially a 12th to a 17th energy waves correspondingly with a 12th to a 17th EDs and in accordance with a 12th to a 17th base frequencies, the 12th ED is 2.23~5.58 and the 12th base frequency is 870~890 Hz, the 13th ED is 2.37~5.93 and the 13th base frequency is 860~880 Hz, the 14th ED is 2.79~6.98 and the 14th base frequency is 800~820 Hz, the 15th ED is 2.89~7.21 and the 15th base frequency is 770~785 Hz, the 16th ED is 2.21~5.51 and the 16th base frequency is 745~765 Hz, the 17th ED is 2.77~6.92 and the 17th base frequency is 720~740 Hz; in the 4th energy wave generation period corresponding to the 4th set of controls, the 4th set of energy waves are sequentially an 18th to a 23rd energy waves correspondingly with an 18th to a 23rd EDs and in accordance with an 18th to a 23rd base frequencies, the 18th ED is 2.17~5.42 and the 18th base frequency is 605~620 Hz, the 19th ED is 2.57~6.41 and the 19th base frequency is 590~610 Hz, the 20th ED is 2.81~7.02 and the 20th base frequency is 535~560 Hz, the 21st ED is 2.14~5.36 and the 21st base frequency is 515~535 Hz, the 22nd ED is 2.48~6.21 and the 22nd base frequency is 476~495 Hz, the 23rd ED is 2.43~6.07 and the 23rd base frequency is 455~475 Hz; in the 5th energy wave generation period corresponding to the 5th set of controls, the 5th set of energy waves are sequentially a 24th to a 28th energy waves correspondingly with a 24th to a 28th EDs and in accordance with a 24th to a 28th base frequencies, the 24th ED is 2.29~5.73 and the 24th base frequency is 295~310 Hz, the 25th ED is 2.18~5.46 and the 25th base frequency is 155~170 Hz, the 26th ED is 2.46 and 6.15 and the 26th base frequency is 135~150 Hz, the 27th ED is 1.90~4.75 and the 27th base frequency is 120~135 Hz, the 28th ED is 1.85~4.63 and the 28th base frequency is 90~110 Hz; in the 6th energy wave generation period corresponding to the 6th set of controls, the 6th set of energy waves are sequentially a 29th to a 33rd energy waves correspondingly with a 29th to a 33rd EDs and in accordance with a 29th to a 33rd base frequencies, the 29th ED is 2.08~5.20 and the 29th base frequency is 10~20 Hz, the 30th ED is 1.41~3.53 and the 30th base frequency is 5~25 Hz, the 31st ED is 1.33~3.33 and the 31st base frequency is 4~15 Hz, the 32nd ED is 0.99~2.47 and the 32nd base frequency is 1~6 Hz, the 33rd ED is 2.05~5.13 and the 33rd base frequency is 25~45 Hz; in the 7th energy wave generation period corresponding to the 7th set of controls, the 7th set of energy waves are sequentially a 34th to a 35th energy waves correspondingly with a 34th to a 35th EDs and in accordance with a 34th to a 35th base frequencies, the 34th ED is 1.45~3.62 and the 34th base frequency is 5~20 Hz, the 35th ED is 1.39~3.48 and the 35th base frequency is 5~15 Hz; in the 8th energy wave generation period corresponding to the 8th set of controls, the 8th set of energy waves are sequentially a 36th to a 37th energy waves correspondingly with a 36th to a 37th EDs and in accordance with a 36th to a 37th base frequencies, the 36th ED is 1.39~3.48 and the 36th base frequency is 5~8 Hz, the 37th ED is 1.45~3.62 and the 37th base frequency is 6~15 Hz; and in the 9th energy wave generation period corresponding to the 9th set of controls, the 9th set of energy waves are sequentially a 38th to a 39th energy waves correspondingly with a 38th to a 39th EDs and in accordance with a 38th to a 39th base frequencies, the 38th ED is 1.79~4.48 and the 38th base frequency is 15~28 Hz, and the 39th ED is 1.41~3.52 and the 39th base frequency is 24~35 Hz.

5. The system for relieving high blood sugar factor of diabetes as claimed in claim 4, wherein the controls based on the 1st to 4th, 6th, 8th to 11th, 12th, 16th, 18th, 21st, 27th, 28th, 30th to 32nd, and 34th to 37th base frequencies, the D %=70%, the Width=0 Hz, and the TT=7, 15, 19, 24, 35, 37, 37, 39, 42, 47, 49, 51, 53, 72, 76, 106, 110, 133, 144, 144, 144 and 144 sees respectively; the controls based on the 5th, 13th, 23rd, 24th and 33rd base frequencies, the D %=70%, the Width=1, 1, 3, 2, and 8 Hz, and the TT=36, 46, 56, 60 and 72 secs respectively; the controls based on the 7th, 14th, 15th, 17th, 20th, 26th and 29th base frequencies, the D %=70%, the Width=7, 7, 9, 7, 9, 6 and 7 Hz respectively, and the TT=30, 45, 57, 45, 57, 65 and 105 secs respectively; the controls based on the 19th, 22nd, 25th, 38th and 39th base frequencies, the D %=70%, the Width=5, 4, 2, 8, and 2 Hz, and the TT=54, 55, 69, 36 and 12 secs respectively.

6. The system for relieving high blood sugar factor of diabetes as claimed in claim 5, wherein the controls based on the 1st to 4th, 6th, 8th to 11th, 12th, 16th, 18th, 21st, 27th, 28th, 30th to 32nd, and 34th to 37th base frequencies are fixed frequency sweep modes respectively; the controls based on the 5th, 13th, 23rd, 24th and 33rd base frequencies are sweep decreasing modes respectively, multiple frequencies being produced and calculated by one predetermined adjusted bandwidth equal to 1 Hz based on each base frequency in each sweep decreasing mode; the controls based on the 7th, 14th, 15th, 17th, 20th, 26th and 29th frequency are spread contract modes respectively, multiple frequencies being produced and calculated by one predetermined adjusted bandwidth equal to 1 Hz based on each base frequency in each spread contract mode; the controls based on the 19th, 22nd, 25th, 38th and 39th base frequencies are sweep increasing modes respectively, multiple frequencies being produced and calculated by one predetermined adjusted bandwidth equal to 1 Hz based on each base frequency in each sweep increasing mode; in the sweep decreasing mode, the first output frequency of the multiple frequencies is calculated as the base frequency plus the Width, the second output frequency of the multiple frequencies is calculated as the first output frequency minus the adjusted bandwidth, and when a current output frequency of the multiple frequencies is equal to the base frequency, the current output frequency is the last output frequency; in the spread contract mode, the first output frequency of the multiple frequencies is calculated as the base frequency minus the Width, the second output frequency of the multiple frequencies is calculated as a base frequency plus the Width, the third output frequency of the multiple frequencies is calculated as the first output frequency plus the adjusted bandwidth, the fourth output frequency of the multiple frequencies is calculated as the second output frequency minus the adjusted bandwidth and so on, and when the current output frequency of the multiple frequencies is equal to the base frequency, the current output frequency is the last output frequency; in the sweep increasing mode, the first output frequency of the multiple frequencies is calculated as the base frequency minus the Width, the second output frequency of the multiple frequencies is calculated as the first output frequency plus the adjusted bandwidth, and when the current output frequency of the multiple frequencies is equal to the base frequency, the current output frequency is the last output frequency.

7. The system for relieving high blood sugar factor of diabetes as claimed in claim 1, wherein the control unit controls the output unit to output the multiple energy waves by switching a direct current≤5 mA on and off in accordance with the frequencies correspondingly.

8. The system for relieving high blood sugar factor of diabetes as claimed in claim 1, wherein a difference of value between two base frequencies of the at least two sets of controls is at least 10000 Hz.

9. The system as claimed in claim 1, wherein the last base frequency of the at least two sets of controls is higher than the last but one base frequency of the at least two sets of controls.

10. The system as claimed in claim 1, wherein the multiple controls further comprises a final set of controls selected from the group consisting of the 1st, 2nd, 3rd, 4th, 5th, 6th, 7th, 8th and 9th sets of controls; and the base frequencies of the final set of controls is higher than the lowest base frequency of the at least two sets of controls.

11. The system for relieving high blood sugar factor of diabetes as claimed in claim 1, wherein at least one base frequency of the at least two sets of controls is between 18150~10001 Hz.

12. A system for relieving high blood sugar factor of diabetes, comprising an energy wave generator, the energy wave generator including a control unit and an output unit, the control unit including an energy wave's frequency control mode for controlling and generating energy waves, the energy wave's frequency control mode including multiple controls configured to operate in multiple energy wave generation periods respectively; according to the multiple controls of the control unit, the energy wave generator configured to generate energy waves in accordance with multiple base frequencies and having multiple energy wave distribution densities (EDs) correspondingly; the energy waves configured to be emitted out by electrode sheets of the output unit configured to effect bodies of diabetic patients to reduce or eliminate high blood sugar factors of diabetes; the energy wave's frequency control mode comprising at least one fixed frequency sweep mode, at least one sweep decreasing mode, at least one spread contract mode and/or at least one sweep increasing mode; the energy wave generator configured to emit energy waves having a decreasing frequency distribution in a predetermined sweep bandwidth by a predetermined adjusted bandwidth in the at least one sweep decreasing mode, to have an increasing frequency distribution in a predetermined sweep bandwidth by a predetermined adjusted bandwidth in the at least one sweep increasing mode, and to have an increasing frequency distribution and a decreasing frequency distribution alternately in a predetermined sweep bandwidth by a predetermined adjusted bandwidth in the at least one spread contract mode; the energy wave distribution density (ED) being calculated by the following formula: $ED = \log_{10}(freq. \times D\% \times (2Width+1) \times (TT)+1)$, wherein freq., Width, D % and TT represent the base frequency, the predetermined sweep bandwidth, an emission rate and a total time of emission in a duty cycle of the base frequency respectively, wherein, the multiple controls configured to be at least two sets of controls selected from the group consisting of a 1st, a 2nd, a 3rd, a 4th, a 5th, a 6th, a 7th, an 8th and a 9th sets of controls; wherein according to the 1st, 2nd, 3rd, 4th, 5th, 6th, 7th, 8th and 9th sets of controls, the energy wave generator in a 1st, a 2nd, a 3rd, a 4th, a 5th, a 6th, a 7th, an 8th and a 9th energy wave generation periods configured to generate a 1st, a 2nd, a 3rd, a 4th, a 5th, a 6th, a 7th, an 8th and a 9th sets of energy waves in accordance with a 1st, a 2nd, a 3rd, a 4th, a 5th, a 6th, a 7th, an 8th and a 9th sets of base frequencies of 4900~18150 Hz, 1230~2130 Hz, 720~890 Hz, 455~620 Hz, 90~310 Hz, 1~45 Hz, 5~20 Hz, 5~15 Hz and 15~35 Hz correspondingly and having a 1st, a 2nd, a 3rd, a 4th, a 5th, a 6th, a 7th, an 8th and a 9th sets of EDs of 2.46~6.28, 2.28~7.25, 2.21~7.21, 2.14~7.02, 1.85~6.15, 0.99~5.20, 1.39~3.62, 1.39~3.62 and 1.41~4.48 correspondingly; and at least one base frequency of the at least two sets of controls being between 18150~10001 Hz.

13. The system as claimed in claim 12, wherein between every two adjacent energy wave generation periods has a non-energy period.

14. The system as claimed in claim 12, wherein in the 1st energy wave generation period corresponding to the 1st set of controls, the 1st set of energy waves are sequentially a 1st to a 4th energy waves correspondingly with a 1st to a 4th EDs and in accordance with a 1st to a 4th base frequencies, the 1st ED is 2.47~6.19 and the 1st base frequency is 18100~18150 Hz, the 2nd ED is 2.51~6.28 and the 2nd base frequency is 9900~10100 Hz, the 3rd ED is 2.49~6.24 and the 3rd base frequency is 7300~7400 Hz, and the 4th ED is 2.46~6.16 and the 4th base frequency is 4900~5100 Hz; in the 2nd energy wave generation period corresponding to the 2nd set of controls, the 2nd set of energy waves are sequentially a 5th to a 11th energy waves correspondingly with a 5th to a 11th EDs and in accordance with a 5th to a 11th base frequencies, the 5th ED is 2.52~6.29 and the 6th base frequency is 2100~2150 Hz, the 6th ED is 2.36~5.89 and the 6th base frequency is 2100~2130 Hz, the 7th ED is 2.90~7.25 and the 7th base frequency is 2000~2015 Hz, the 8th ED is 2.34~5.85 and the 8th base frequency is 1860~1880 Hz, the 9th ED is 2.34~5.85 and the 9th base frequency is 1845~1855 Hz, the 10th ED is 2.31~5.78 and the 10th base frequency is 1540~1560 Hz, the 11th ED is 2.28~5.70 and the 11th base frequency is 1230~1245 Hz; in the 3rd energy wave generation period corresponding to the 3rd set of controls, the 3rd set of energy waves are sequentially a 12th to a 17th energy waves correspondingly with a 12th to a 17th EDs and in accordance with a 12th to a 17th base frequencies, the 12th ED is 2.23~5.58 and the 12th base frequency is 870~890 Hz, the 13th ED is 2.37~5.93 and the 13th base frequency is 860~880 Hz, the 14th ED is 2.79~6.98 and the 14th base frequency is 800~820 Hz, the 15th ED is 2.89~7.21 and the 15th base frequency is 770~785 Hz, the 16th ED is 2.21~5.51 and the 16th base frequency is 745~765 Hz, the 17th ED is 2.77~6.92 and the 17th base frequency is 720~740 Hz; in the 4th energy wave generation period corresponding to the 4th set of controls, the 4th set of energy waves are sequentially an 18th to a 23rd energy waves correspondingly with an 18th to a 23rd EDs and in accordance with an 18th to a 23rd base frequencies, the 18th ED is 2.17~5.42 and the 18th base frequency is 605~620 Hz, the 19th ED is 2.57~6.41 and the 19th base frequency is 590~610 Hz, the 20th ED is 2.81~7.02 and the 20th base frequency is 535~560 Hz, the 21st ED is 2.14~5.36 and the 21st base frequency is 515~535 Hz, the 22nd ED is 2.48~6.21 and the 22nd base frequency is 476~495 Hz, the 23rd ED is 2.43~6.07 and the 23rd base frequency is 455~475 Hz; in the 5th energy wave generation period corresponding to the 5th set of controls, the 5th set of energy waves are sequentially a 24th to a 28th energy waves correspondingly with a 24th to a 28th EDs and in accordance with a 24th to a 28th base frequencies, the 24th ED is 2.29~5.73 and the 24th base frequency is 295~310 Hz, the 25th ED is 2.18~5.46 and the 25th base frequency is 155~170 Hz, the 26th the ED is 2.46 and 6.15 and the 26th base frequency is 135~150 Hz, the 27th ED is 1.90~4.75 and the 27th base frequency is 120~135 Hz, the 28th ED is 1.85~4.63 and the 28th base frequency is 90~110 Hz; in the 6th energy wave generation period corresponding to the 6th set of controls, the 6th set of energy waves are sequentially a 29th to a 33rd energy waves correspondingly with a 29th to a 33rd EDs and in accordance with a 29th to a 33rd base frequencies, the 29th ED is 2.08~5.20 and the 29th base frequency is 10~20 Hz, the 30th ED is 1.41~3.53 and the 30th base frequency is 5~25 Hz, the 31st ED is 1.33~3.33 and the 31st base frequency is 4~15 Hz, the 32nd ED is 0.99~2.47 and the 32nd base frequency is 1~6 Hz, the 33rd ED is 2.05~5.13 and the 33rd base frequency is 25~45 Hz in the 7th energy wave generation period corresponding to the 7th set of controls, the 7th set of energy waves are sequentially a 34th to a 35th energy waves correspondingly with a 34th to a 35th EDs and in accordance with a 34th to a 35th base frequencies, the 34th ED is 1.45~3.62 and the 34th base frequency is 5~20 Hz, the 35th ED is 1.39~3.48 and the 35th base frequency is 5~15 Hz; in the 8th energy wave generation period corresponding to the 8th set of controls, the 8th set of energy waves are sequentially a 36th to a 37th energy waves correspondingly with a 36th to a 37th EDs and in accordance with a 36th to a 37th base frequencies, the 36th ED is 1.39~3.48 and the 36th base frequency is 5~8 Hz, the 37th ED is 1.45~3.62 and the 37th base frequency is 6~15 Hz; and in the 9th energy wave generation period corresponding to the 9th set of controls, the 9th set of energy waves are sequentially a 38th to a 39th energy waves correspondingly with a 38th to a 39th EDs and in accordance with a 38th to a 39th base frequencies, the 38th ED is 1.79~4.48 and the 38th base frequency is 15~28 Hz, and the 39th ED is 1.41~3.52 and the 39th base frequency is 24~35 Hz.

15. The system as claimed in claim 14, wherein the controls based on the 1st to 4th, 6th, 8th to 11th, 12th, 16th, 18th, 21st, 27th, 28th, 30th to 32nd, and 34th to 37th base frequencies, the D %=70%, the Width=0 Hz, and the TT=7, 15, 19, 24, 35, 37, 37, 39, 42, 47, 49, 51, 53, 72, 76, 106, 110, 133, 144, 144, 144 and 144 secs respectively; in the controls based on the 5th, 13th, 23rd, 24th and 33rd base frequencies, the D %=70%, the Width=1, 1, 3, 2, and 8 Hz, and the TT=36, 46, 56, 60 and 72 secs respectively; the controls based on the 7th, 14th, 15th, 17th, 20th, 26th and 29th base frequencies, the D %=70%, the Width=7, 7, 9, 7, 9, 6 and 7 Hz respectively, and the TT=30, 45, 57, 45, 57, 65 and 105 secs respectively; the controls based on the 19th, 22nd, 25th, 38th and 39th base frequencies, the D %=70%, the Width=5, 4, 2, 8, and 2 Hz, and the TT=54, 55, 69, 36 and 12 secs respectively.

16. The system as claimed in claim 14, wherein the controls based on the 1st to 4th, 6th, 8th to 11th, 12th, 16th, 18th, 21st, 27th, 28th, 30th to 32nd, and 34th to 37th base frequencies are fixed frequency sweep modes respectively; the controls based on the 5th, 13th, 23rd, 24th and 33rd base frequencies are sweep decreasing modes respectively, multiple frequencies being produced and calculated by one predetermined adjusted bandwidth equal to 1 Hz based on each base frequency in each sweep decreasing mode; the controls based on the 7th, 14th, 15th, 17th, 20th, 26th and 29th frequency are spread contract modes respectively, multiple frequencies being produced and calculated by one predetermined adjusted bandwidth equal to 1 Hz based on each base frequency in each spread contract mode; the controls based on the 19th, 22nd, 25th, 38th and 39th base frequencies are sweep increasing modes respectively, multiple frequencies being produced and calculated by one predetermined adjusted bandwidth equal to 1 Hz based on each base frequency in each sweep increasing mode; in the sweep decreasing mode, the first output frequency of the multiple frequencies is calculated as the base frequency plus the Width, the second output frequency of the multiple frequencies is calculated as the first output frequency minus the adjusted bandwidth, and when a current output frequency of the multiple frequencies is equal to the base frequency, the current output frequency is the last output frequency; in the spread contract mode, the first output frequency of the multiple frequencies is calculated as the base frequency minus the Width, the second output frequency of the multiple frequencies is calculated as the base frequency plus the Width, the third output frequency of the multiple frequencies is calculated as the first output frequency plus the adjusted bandwidth, the fourth output frequency of the multiple frequencies is calculated as the second output frequency minus the adjusted bandwidth and so on, and when the current output frequency of the multiple frequencies is equal to the base frequency, the current output frequency is the last output frequency; in the sweep increasing mode, the first output frequency of the multiple frequencies is calculated as the base frequency minus the Width, the second output frequency of the multiple frequencies is calculated as the first output frequency plus the adjusted bandwidth, and when the current output frequency of the multiple frequencies is equal to the base frequency, the current output frequency is the last output frequency.

* * * * *